United States Patent
Nakai et al.

(10) Patent No.: US 11,892,104 B2
(45) Date of Patent: Feb. 6, 2024

(54) FLEXIBLE TUBE FOR ENDOSCOPES AND METHOD FOR PRODUCING SAME

(71) Applicant: FUJIFILM Corporation, Tokyo (JP)

(72) Inventors: Yoshihiro Nakai, Ashigarakami-gun (JP); Kiyotaka Fukagawa, Ashigarakami-gun (JP); Nobuharu Takahashi, Ashigarakami-gun (JP); Kazuya Takeuchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/566,178

(22) Filed: Dec. 30, 2021

(65) Prior Publication Data

US 2022/0119675 A1    Apr. 21, 2022

Related U.S. Application Data

(63) Continuation of application No. 14/857,396, filed on Sep. 17, 2015, now abandoned, which is a
(Continued)

(30) Foreign Application Priority Data

Mar. 27, 2013  (JP) .................................. 2013-067194
Jul. 12, 2013  (JP) ................................. 2013-147104

(51) Int. Cl.
*F16L 11/04*    (2006.01)
*C08L 75/04*    (2006.01)
(Continued)

(52) U.S. Cl.
CPC .............. *F16L 11/04* (2013.01); *A61B 1/005* (2013.01); *A61B 1/0011* (2013.01); *B32B 1/08* (2013.01);
(Continued)

(58) Field of Classification Search
None
See application file for complete search history.

(56) References Cited

U.S. PATENT DOCUMENTS 4,542,165 A    9/1985   Kumata et al.
6,037,423 A    3/2000   Nagano et al.
(Continued)

FOREIGN PATENT DOCUMENTS

DE    10062000 A1    6/2001
DE    10122203 A1    1/2002
(Continued)

OTHER PUBLICATIONS

Chanda M et al., Plastic Fundamentals, Properties, and Testing, CRC Press, Boca Raton, p. 1-84. (Year: 2008).*
(Continued)

*Primary Examiner* — Lee E Sanderson
(74) *Attorney, Agent, or Firm* — Sughrue Mion, PLLC

(57) ABSTRACT

An endoscope flexible tube having a cylindrical flexible tube base that has flexibility and a resin layer that coats the flexible tube base includes the resin layer, which is a single layer or multiple layers of two or more layers, comprises a layer A which comprises: polyester elastomers, at least one of polyurethane elastomers or polyamide elastomers, and both a hindered phenol compound and a hindered amine compound, wherein the content of the polyester elastomers in the layer A is 55 mass % or more.

12 Claims, 4 Drawing Sheets

Related U.S. Application Data continuation of application No. PCT/JP2014/058611, filed on Mar. 26, 2014.

(51) Int. Cl.

| | | |
|---|---|---|
| *C08L 67/00* | (2006.01) | |
| *A61B 1/00* | (2006.01) | |
| *B32B 1/08* | (2006.01) | |
| *B32B 25/08* | (2006.01) | |
| *A61B 1/005* | (2006.01) | |
| *C09D 167/00* | (2006.01) | |
| *C09D 175/04* | (2006.01) | |
| *C09D 177/00* | (2006.01) | |
| *C08K 5/3435* | (2006.01) | |
| *C08L 77/00* | (2006.01) | |
| *C08K 5/13* | (2006.01) | |

(52) U.S. Cl.
CPC .............. *B32B 25/08* (2013.01); *C08L 67/00* (2013.01); *C08L 75/04* (2013.01); *C09D 167/00* (2013.01); *C09D 175/04* (2013.01); *C09D 177/00* (2013.01); *B32B 2597/00* (2013.01); *C08K 5/13* (2013.01); *C08K 5/3435* (2013.01); *C08L 77/00* (2013.01)

(56) References Cited

U.S. PATENT DOCUMENTS

| | | | |
|---|---|---|---|
| 6,187,859 | B1 | 2/2001 | Humphrey et al. |
| 6,242,097 | B1 | 6/2001 | Nishiguchi et al. |
| 6,599,239 | B2 | 7/2003 | Hayakawa et al. |
| 6,860,849 | B2 | 3/2005 | Matsushita et al. |
| 7,169,105 | B2 | 1/2007 | Iwasaka et al. |
| 8,580,063 | B2 * | 11/2013 | Koori ................. A61B 1/00071 156/169 |
| 2001/0007917 | A1 | 7/2001 | Hayakawa et al. |
| 2002/0010386 | A1 | 1/2002 | Matsushita et al. |
| 2004/0193013 | A1* | 9/2004 | Iwasaka .................... B32B 3/30 600/140 |
| 2009/0198021 | A1 | 8/2009 | Ogura et al. |
| 2009/0246434 | A1 | 10/2009 | Miyamoto |
| 2010/0075075 | A1 | 3/2010 | Takahashi |
| 2012/0180896 | A1* | 7/2012 | Takahashi ............ A61B 1/0056 427/2.12 |
| 2014/0079898 | A1* | 3/2014 | Kaushik ............... C09D 167/02 524/359 |

FOREIGN PATENT DOCUMENTS

| | | | |
|---|---|---|---|
| EP | 2106904 | A1 | 10/2009 |
| EP | 2168471 | A2 | 3/2010 |
| JP | 02-283346 | A | 11/1990 |
| JP | 10182963 | | 7/1998 |
| JP | 10231415 | A | 9/1998 |
| JP | 2001-161633 | A | 6/2001 |
| JP | 2001314368 | A | 11/2001 |
| JP | 2001321324 | A | 11/2001 |
| JP | 2002-153418 | A | 5/2002 |
| JP | 2002153418 | A * | 5/2002 |
| JP | 2004-195833 | A | 7/2004 |
| JP | 2004-202844 | A | 7/2004 |
| JP | 2004-269608 | A | 9/2004 |
| JP | 2009-183467 | A | 8/2009 |
| JP | 2009262545 | A | 11/2009 |
| JP | 2010075352 | A | 4/2010 |
| JP | 2011-067383 | A | 4/2011 |
| JP | 2011-072391 | A | 4/2011 |
| JP | 2011-095480 | A | 5/2011 |
| JP | 2011122019 | A | 6/2011 |

OTHER PUBLICATIONS

English Translation of communication from the State Intellectual Property Office of the P.R.C. dated May 31, 2016 in Chinese application No. 201480018577.3. (Original Office Action Submitted Jul. 18, 2016).
Communication dated Mar. 30, 2016, from the European Patent Office in European Application No. 14775365.1.
Communication dated Mar. 7, 2018, from the European Patent Office in European Application No. 14 775 365.1.
International Preliminary Report on Patentability and Written Opinion, dated Sep. 29, 2015, in corresponding International Application No. PCT/JP2014/058611, 12 pages in English and Japanese.
Communication dated Apr. 19, 2016 issued by the Japanese Patent Office in Japanese application No. 2013-067194.
Communication dated Apr. 19, 2016 issued by the Japanese Patent Office in Japanese application No. 2013-147104.
Communication dated May 31, 2016 issued by the Chinese Patent Office in Chinese application No. 201480018577.3.
International Search Report for PCT/JP2014/058611 dated Jun. 24, 2014 [PCT/ISA/210].
Written Opinion for PCT/JP2014/058611 dated Jun. 24, 2014 [PCT/ISA/237].

* cited by examiner

FLEXIBLE TUBE FOR ENDOSCOPES AND METHOD FOR PRODUCING SAME

CROSS-REFERENCE TO RELATED APPLICATIONS

This application is a Continuation of U.S. application Ser. No. 14/857,396 filed on Sep. 17, 2015, which is a Continuation of PCT International Application No. PCT/JP2014/058611 filed on Mar. 26, 2014, which claims priority under 35 U.S.C § 119(a) to Japanese Patent Application No. 2013-067194 filed on Mar. 27, 2013 and Japanese Patent Application No. 2013-147104 filed on Jul. 12, 2013. Each of the above application(s) is hereby expressly incorporated by reference, in its entirety, into the present application.

BACKGROUND OF THE INVENTION

1. Field of the Invention

The present invention relates to a flexible tube for an endoscope and a method for producing the same.

2. Description of the Related Art

An endoscope is medical device for observing a body cavity of a patient. Accordingly, since endoscopes are used by being inserted into a body cavity, there is a demand for endoscopes which do not damage organs and which do not cause pain or discomfort to the patient. As a result of these demands, a spiral tube which is formed by winding a metal strip which bends softly in a spiral form is adopted for the flexible tube which configures the insertion unit of the endoscope. Furthermore, the periphery of the flexible tube is coated with a soft resin and is designed so as not to irritate or damage the surface of the esophagus, intestines, or the like.

A layer of the soft resin can be formed by extruding and molding the resin onto an outer peripheral surface of a flexible tube base formed by covering the spiral tube with a cylindrical net body. At that time, it is preferable to make the front end side soft by increasing the flexibility in order to make it easy to insert the insertion unit into a body cavity, while making the rear end side hard by reducing the flexibility in order to improve operability. Taking this into consideration, the present applicant proposed adopting a double layer structure with an inner layer and an outer layer which have different hardnesses from each other as the resin layer and changing the ratio of the thicknesses of the inner layer and the outer layer of the resin layer in the axial direction of the flexible tube (refer to JP2011-72391 A). Due to this, the balance of the hardness is made to be favorable over the entire flexible tube by changing the flexibility in the axial direction of the flexible tube and the demands described above are met.

Since endoscopes are used repeatedly, it is necessary to clean the endoscopes after each use and sterilize the endoscopes using chemicals. Chemicals which have a strong effect on the endoscope material are generally used. For this reason, some techniques for improving the chemical resistance of the endoscope are also known. For example, JP2009-183467A describes an elastomer molded body formed by two or more types of thermoplastic polyester elastomers being cross-linked. The resistance of the flexible tube with respect to a peracetic acid aqueous solution is improved by forming the resin layer of the flexible tube using the molded body.

In addition, JP2002-153418A discloses forming a resin layer of a flexible tube using a resin with a structure in which urethane-based polymers and ester-based polymers are cross-linked. JP2002-153418A describes that the solubility of the resin layer with respect to chemicals such as N,N-dimethyl formamide is suppressed due to this.

SUMMARY OF THE INVENTION

Problem According to First Invention

An object of the development by the present applicant is to add further improvements to the resin layer of the endoscope flexible tube with a double layer structure developed in JP2011-72391A described above and to improve the total performance which is required for an endoscope. In particular, resin blends were investigated while taking into consideration not only the basic physical properties of the resins, such as flexibility or elasticity, but also points such as resistance with respect to cleaning after diagnosis or temperature dependency, which affects fine operability during a diagnosis by a physician.

Then, an object of the present first invention is to provide a flexible tube for an endoscope and a method for producing the same in which a resin layer provided on the flexible tube for an endoscope maintains favorable resin physical properties that are required for medical use, such as flexibility, has high resistance with respect to cleaning liquids, suppresses changes in the physical properties due to temperature (temperature dependency), and has excellent top coat adhesion.

Problem According to Second Invention

When considering achieving both durability with respect to disinfectants and the various performances which are required for a flexible tube, it is not clear whether the techniques of each of JP2011-72391A, JP2009-183467A, and JP2002-153418A were sufficient. In consideration of the points described above, an object of the present embodiment is to provide a flexible tube and an endoscope using the same which is provided with basic characteristics, such as flexibility, elasticity, and bending durability required for flexible tubes used for endoscope type medical devices, and which exhibits favorable resistance with respect to various types of disinfectant liquids.

The objects described above were achieved by the following means.

[1] A flexible tube which has a cylindrical flexible tube base that has flexibility and a resin layer that coats the flexible tube base, in which the resin layer is configured by at least two layers of a first layer and a second layer, in which the first layer includes one or more elastomers or chain-extended forms thereof selected from a group consisting of polyester elastomers, polyurethane elastomers, and polyamide elastomers, and in which the second layer includes chain-extended forms of two or more elastomers selected from a group consisting of polyester elastomers, polyurethane elastomers, and polyamide elastomers.

[2] The flexible tube described in [1], in which a chain extender for preparing the chain-extended forms of the elastomers is selected from polyfunctional epoxy compounds, polyfunctional isocyanate compounds, polyfunctional amino compounds, oxazoline compounds, carbodiimide compounds, and acid anhydrides.

[3] The flexible tube described in [2], in which the chain-extended form of the elastomer is obtained by adding at least one catalyst selected from amine compounds and tin chelate to the elastomer in addition to the chain extender.

[4] The flexible tube described in [2] or [3], in which the chain-extended form of the elastomer is obtained by adding 0.01 to 10 parts by mass of the chain extender with respect to 100 parts by mass of the elastomer.

[5] The flexible tube described in [3] or [4], in which the chain-extended form of the elastomer is obtained by adding 0.01 to 3 parts by mass of the catalyst with respect to 100 parts by mass of the elastomer.

[6] The flexible tube described in any one of [1] to [5], in which the elastomer is melt-kneaded with at least the chain extender.

[7] The flexible tube described in any one of [1] to [6], in which two or more of the elastomers which configure the second layer are a combination of polyester elastomers and at least one selected from polyurethane elastomers and polyamide elastomers.

[8] The flexible tube described in any one of [1] to [7], in which the resin layer is soluble in 1,1,1,3,3,3-hexafluoro-2-propanol and substantially not cross-linked.

[9] The flexible tube described in any one of [1] to [8], in which the first layer of the resin layer is an inner layer which coats an entire peripheral surface around an axis of the flexible tube base, and the second layer is an outer layer which contacts the first layer and coats an entire peripheral surface around an axis of the first layer.

[10] The flexible tube described in any one of [1] to [9], in which a heat stabilizer which is selected from phenol-based compounds, amine-based compounds, phosphorus-based compounds, sulfur-based compounds, and phenylacrylate-based compounds is further contained in the resin layer.

[11] A flexible tube which has a cylindrical flexible tube base that has flexibility and a resin layer that coats the flexible tube base, in which the resin layer is a single layer or multiple layers of two or more layers, and a layer A which is any out of the resin layers includes polyester elastomers, and, hindered phenol compounds or hindered amine compounds.

[12] The flexible tube described in [11], in which the content of the polyester elastomers in a resin component is 50 mass % or more in the layer A.

[13] The flexible tube described in [11] or [12], in which the layer A further contains polyurethane elastomers or polyamide elastomers.

[14] The flexible tube described in any one of [11] to [13], in which the layer A contains both hindered phenol compounds and hindered amine compounds.

[15] The flexible tube described in any one of [11] to [14], in which the content of the hindered phenol compounds is 0.01 to 5 parts by mass with respect to 100 parts by mass of a resin component in the resin layer.

[16] The flexible tube described in any one of [11] to [14], in which the content of the hindered amine compounds is 0.01 to 5 parts by mass with respect to 100 parts by mass of a resin component in the resin layer.

[17] The flexible tube described in any one of [11] to [16], in which the hindered phenol compounds have structure sites which are represented by the following Formula (1) and the hindered amine compounds have structure sites which are represented by the following Formula (2),

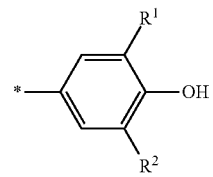
(1)

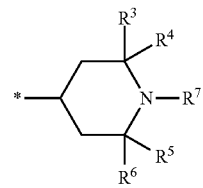
(2)

(where, $R^1$ and $R^2$ each independently indicate a hydrogen atom, an alkyl group having 1 to 12 carbon atoms, or an aralkyl group having 7 to 36 carbon atoms, $R^3$ to $R^6$ each independently indicate a hydrogen atom or an alkyl group having 1 to 12 carbon atoms, $R^7$ indicates a hydrogen atom, an alkyl group having 1 to 18 carbon atoms, or —$OR^8$, $R^8$ indicates a hydrogen atom or an alkyl group having 1 to 20 carbon atoms, and * indicates a bonding position).

[18] The flexible tube described in [17], in which the hindered phenol compounds are represented by the following Formula (1-1) or (1-2),

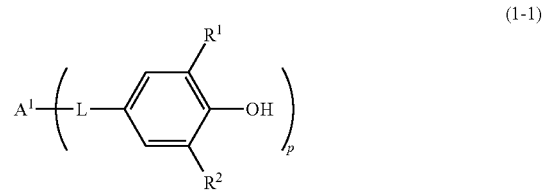
(1-1)

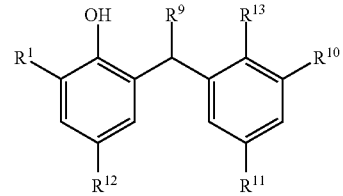
(1-2)

(where, $R^1$ and $R^2$ are the same as in Formula (1), L indicates a single bond or a divalent linking group, p indicates an integer of 2 to 4, $A^1$ indicates a divalent to tetravalent linking group, $R^9$ to $R^{12}$ are the same as $R^1$, and $R^{13}$ represents a reactive organic substituent group).

[19] The flexible tube described in [17], in which the hindered amine compounds are compounds represented by the following Formula (2-1) or compounds which have repeating units represented by (2-2),

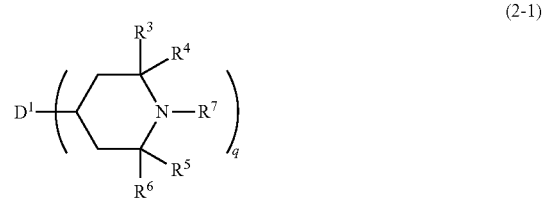
(2-1)

-continued

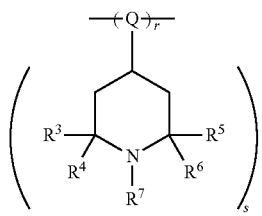

(2-2)

(where, $R^3$ to $R^7$ are the same as in Formula (2), q indicates an integer of 2 or greater, $D^1$ indicates a divalent or higher linking group, r represents an integer, Q represents an (s+2)-valent linking group, and s represents 1 or 2).

[20] The flexible tube described in any one of [11] to [19], in which the resin layer is multiple layers and the layer A configures an outermost layer of the resin layer.

[21] The flexible tube described in [20], in which a layer B other than the outermost layer contains at least one resin which is selected from polyester elastomers, polyurethane elastomers, and polyamide elastomers.

[22] The flexible tube described in [21], in which the content of polyurethane elastomers in a resin component of the layer B is 50 mass % or more.

[23] The flexible tube described in [21] or [22], in which the layer B contains hindered phenol compounds or hindered amine compounds.

[24] The flexible tube described in any one of [11] to [23], in which the resin layer is formed of two layers.

[25] The flexible tube described in [24], in which a ratio of thicknesses of an inner layer and an outer layer incrementally changes in an axial direction of the flexible tube base with respect to a thickness of the entire resin layer.

[26] The flexible tube described in [25], in which a ratio of the thicknesses of the inner layer and the outer layer at one end of the flexible tube base is Inner layer:Outer layer=5:95 to 40:60, a ratio of the thicknesses at another end of the flexible tube base is Inner layer:Outer layer=95:5 to 60:40, and the ratio of the thicknesses is reversed between both ends.

[27] The flexible tube described in any one of [11] to [26], which is for an endoscope type medical device.

[28] An endoscope type medical device including: the flexible tube described in any one of [11] to [27].

[29] A method for producing a flexible tube which has a cylindrical flexible tube base that has flexibility and a resin layer that coats the flexible tube base, in which the resin layer is configured by at least two layers of a first layer and a second layer, and in which the method includes: preparing a first resin material which includes polyester elastomers, polyurethane elastomers, or polyamide elastomers for configuring the first layer, preparing a second resin material which contains two or more elastomers which are selected from a group consisting of polyester elastomers, polyurethane elastomers, and polyamide elastomers, and a chain extender, for configuring the second layer; and melt-kneading, extruding and molding the first resin material and the second resin material respectively in the periphery of the flexible tube base to coat the flexible tube base with the resin layer.

[30] The method for producing the flexible tube described in [29], in which at least one chain extender which is selected from polyfunctional epoxy compounds, polyfunctional isocyanate compounds, polyfunctional amino compounds, oxazoline compounds, carbodiimide compounds, and acid anhydrides is used as the chain extender.

[31] The method for producing the flexible tube described in [29] or [30], in which at least one catalyst which is selected from amine compounds and tin chelate is further contained in the first resin material and/or the second resin material.

[32] A resin composition which forms a resin layer that coats a flexible tube base, the composition including: polyester elastomers, and, hindered phenol compounds or hindered amine compounds.

[33] A set of resin compositions which form a plurality of resin layers that coat a flexible tube base including a combination of a resin composition which includes polyester elastomers, and, hindered phenol compounds or hindered amine compounds, and a resin composition which includes at least one which is selected from polyester elastomers, polyurethane elastomers, and polyamide elastomers.

In the present specification, when there are a plurality of substituent groups, linking groups, or the like (referred to below as substituent groups and the like) which are shown with specific reference numerals or when a plurality of substituent groups and the like are regulated at the same time or selectively, this has the meaning that each of the substituent groups and the like may be the same as each other or may be different from each other. In addition, even when not particularly mentioned, when the plurality of the substituent groups and the like are adjacent, this has the meaning that these groups and the like may form a ring by linking with each other or being condensed.

In the present specification, with regard to substituent groups (the same also applies to linking groups) which are not clearly specified as substituted or unsubstituted, this has the meaning that the groups may have arbitrary substituent groups in a range in which the desired effects are exhibited. The same also applies to compounds which are not clearly specified as substituted or unsubstituted.

With regard to a flexible tube for an endoscope of the present first invention, the coated resin layer maintains physical properties, such as flexibility, which are required for endoscope use, has high resistance with respect to cleaning liquids, suppresses changes in physical properties according to temperature (temperature dependency), and has excellent top coat adhesion. According to the production method of the present embodiment, it is possible to favorably produce a flexible tube for an endoscope which exhibits the excellent performances described above.

With regard to a flexible tube which is used for an endoscope type medical device and the like of the present second invention and an endoscope which uses the same, a resin layer which coats the flexible tube is provided with characteristics, such as flexibility, elasticity, and bending durability, which are required for endoscope use and exhibits favorable resistance with respect to various types of disinfectant liquids.

The description above, other features, and advantages of the present invention will become clear from the following description and attached diagrams.

DESCRIPTION OF THE PREFERRED EMBODIMENTS

Figure 1:
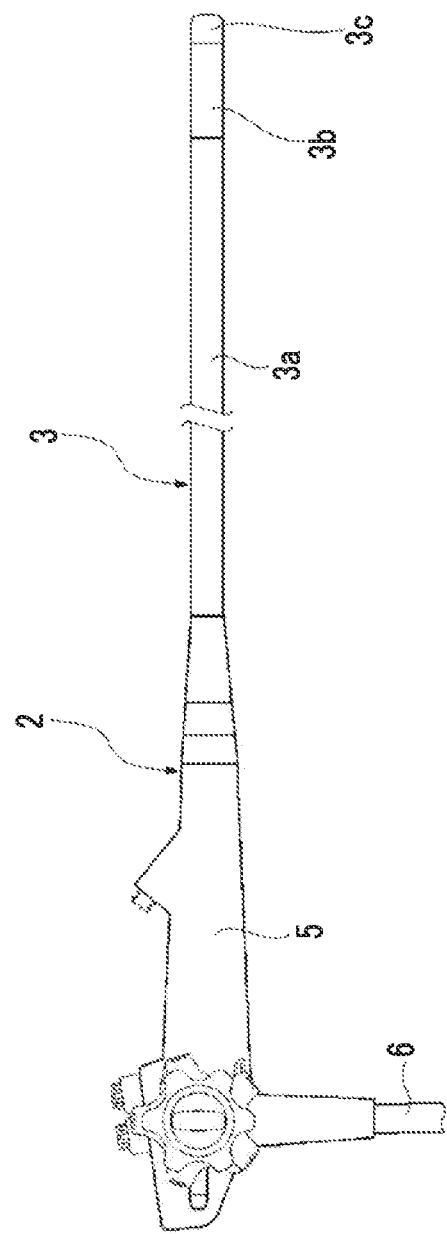
FIG. 1 is an outline diagram which shows a configuration of an electronic endoscope.

A flexible tube is incorporated into an electronic endoscope according to a preferable embodiment of the present invention. Such products are widely used for medical procedures. In the example shown in FIG. 1, an electronic endoscope 2 is provided with an insertion unit 3 which is inserted into a body cavity, a main body operation section 5 which is continuous with a base end portion of the insertion unit 3, and a universal cord 6 which is connected with a processor apparatus or a light source device. The insertion unit 3 is configured from a flexible tube 3a which is continuous with the main body operation section 5, an angle section 3b which is continuous therewith, and a tip portion 3c which is continuous with the front end thereof and in which an imaging apparatus for imaging a body cavity (which is not shown in the diagram) is installed. The flexible tube 3a which accounts for the majority of the length of the insertion unit 3 has flexibility over substantially the whole length thereof and, in particular, the portion which is inserted inside a body cavity or the like has a more flexible structure.

Flexible Tube

Figure 2:
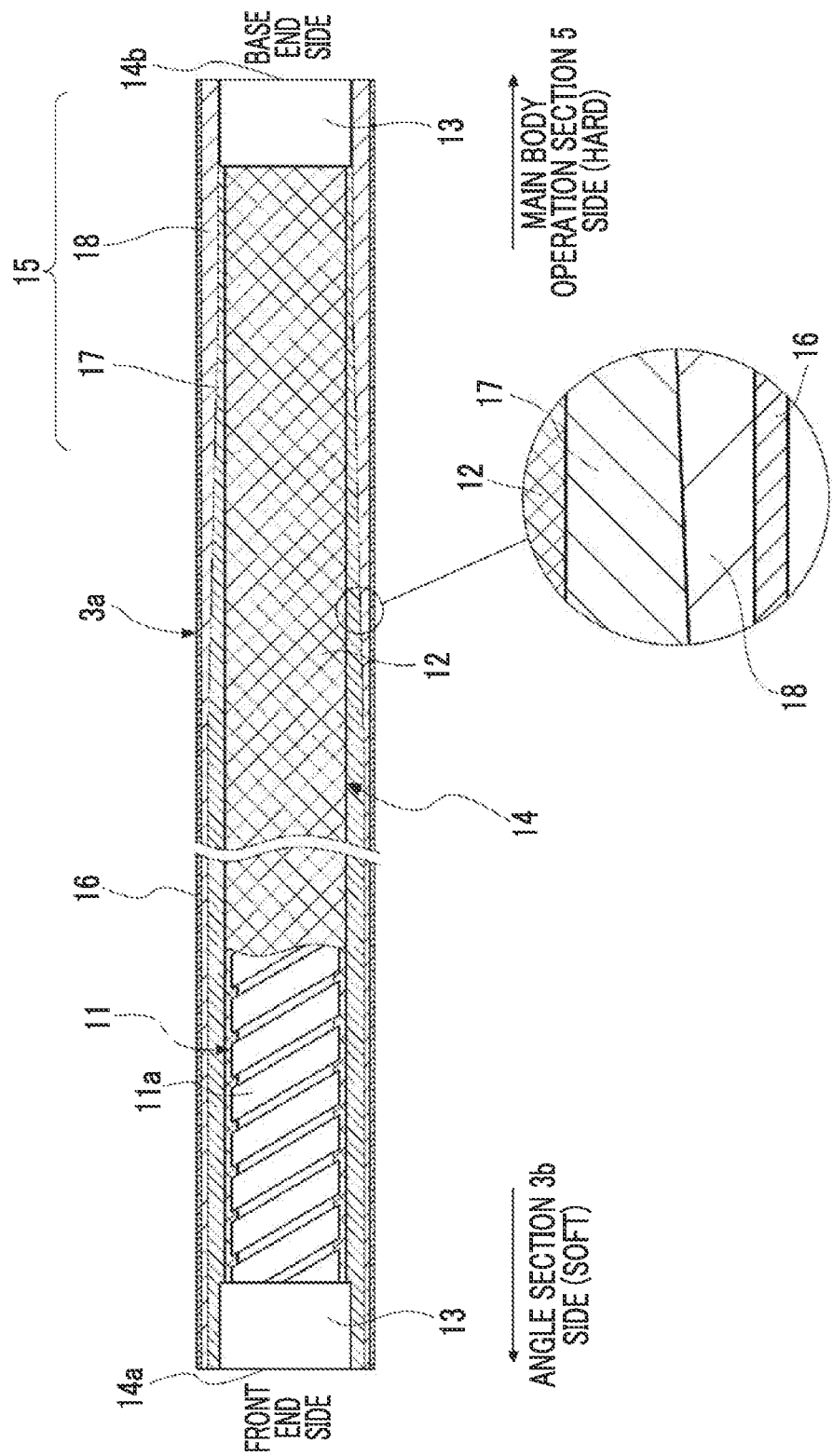
FIG. 2 is a partial sectional diagram which shows a schematic configuration of a flexible tube.

As shown in FIG. 2, the flexible tube 3a (a flexible tube for an endoscope) is configured by a flexible tube base 14 where a spiral tube 11 formed by spirally winding a metal strip 11a on the innermost side is coated with a cylindrical net body 12 formed by braiding metal lines and metal caps 13 are respectively fitted on both ends, and a resin layer 15 is further coated over the peripheral surface thereof. In addition, a coating layer 16 which contains, for example, fluorine or the like which has chemical resistance is coated on the outer surface of the resin layer 15. The spiral tube 11 has only one layer in the diagram, but may be configured by laminating another layer on the same axis. Here, the resin layer 15 and the coating layer 16 are drawn thicker in comparison with the diameter of the flexible tube base 14 in order to clearly illustrate the layer structure.

The resin layer 15 according to the present embodiment coats the outer peripheral surface of the flexible tube base 14. The resin layer 15 has a double layer configuration in which an inner layer 17 which coats the entire peripheral surface surrounding the axis of the flexible tube base 14 and an outer layer 18 which coats the entire peripheral surface surrounding the axis of the inner layer 17 are laminated. A soft resin is used as the material of the inner layer 17 and a hard resin is used as the material of the outer layer 18.

In the present embodiment, the resin layer 15 is formed with a substantially uniform thickness in the longitudinal direction (the axial direction) of the flexible tube base 14. The thickness of the resin layer 15 is, for example, 0.2 mm to 1.0 mm and an outer diameter D of the flexible tube 3a is, for example, 11 mm to 14 mm. The thicknesses of the inner layer 17 and the outer layer 18 are formed such that the ratio of the thicknesses of each of the layers 17 and 18 changes with respect to the thickness of the resin layer 15 as a whole in the axial direction of the flexible tube base 14. In detail, on one end 14a side (the front end side) of the flexible tube base 14 which is attached to the angle section 3b, the thickness of the inner layer 17 is greater than the thickness of the outer layer 18 with respect to the entire thickness of the resin layer 15. Then, the thickness of the inner layer 17 gradually decreases from the one end 14a toward the other end 14b side (a base end side) which is attached to the main body operation section 5 and the thickness of the outer layer 18 is greater than the inner layer 17 on the other end 14b side.

The ratio of the thicknesses of the inner layer 17 and the outer layer 18 is the maximum at both of the ends 14a and 14b in the present embodiment, and is 9:1 at the one end 14a and 1:9 at the other end 14b. Between both of the ends 14a and 14b, the ratio of the thicknesses of the inner layer 17 and the outer layer 18 changes so as to be reversed. Due to this, with regard to the flexible tube 3a, the flexibility changes in the axial direction such that a difference in hardness is generated between the one end 14a side and the other end 14b side with the one end 14a side being soft, and the other end 14b side being hard. With regard to the inner layer and the outer layer, the ratio of the thicknesses at one end is preferably 5:95 to 40:60 (inner layer-outer layer) and the ratio of the thicknesses at the other end is preferably in the range of 95:5 to 60:40 (inner layer:outer layer).

Here, the ratio of the thicknesses of the inner layer 17 and the outer layer 18 is preferably within the range of 5:95 to 95:5 as the example described above. Within this range, it is also possible to control the extruded amount of thinner resins more precisely.

With regard to a soft resin and a hard resin used for the inner layer 17 and the outer layer 18, the difference in the 100% modulus value, which is an index which represents hardness after molding, is preferably 1 MPa or more, and more preferably 3 MPa or more. When the difference is greater, 10 MPa or more is preferable. A difference in the melt viscosity at a molding temperature of 150° C. to 300° C. which is an index which represents the fluidity of a resin in a melted state is preferably 2,500 PaS or less. Due to this, for the resin layer 15 formed of the inner layer 17 and the outer layer 18, favorable molding precision is secured along with the necessary hardness difference between the front end side and the base end side.

Method for Producing Flexible Tube

With regard to a production method according to a preferable embodiment of the first invention, when forming a resin layer which is configured by at least two layers of a first layer and a second layer, it is preferable that (i) a first resin material which includes polyester elastomers, polyurethane elastomers, or polyamide elastomers for configuring the first layer is prepared, on the other hand, (ii) a second resin material which contains two or more elastomers which are selected from a group consisting of polyester elastomers, polyurethane elastomers, and polyamide elastomers and a chain extender for configuring the second layer are prepared, and (iii) the first resin material and the second resin material are melt-kneaded, extruded, and molded in the periphery of the flexible tube base and the flexible tube base is coated with the resin layer.

Description will be given below of an example of a method for producing a flexible tube with a double layer structure in which a resin layer is formed of an inner layer and an outer layer including the second invention; however, it is also possible to produce aspects where the resin layer is one layer or three or more layers according to the following methods.

When forming a resin layer which is configured by at least two layers of an inner layer and an outer layer, it is preferable that (i) a first resin material which configures the inner layer is prepared, on the other hand, (ii) a second resin material which configures the outer layer is prepared, and (iii) the first resin material and the second resin material are melt-kneaded, extruded, and molded in the periphery of the flexible tube base and the flexible tube base is coated with the resin layer.

Description will be given of a method for producing the flexible tube 3a (FIGS. 1 and 2) based on FIGS. 3 and 4. A consecutive molding machine is preferably used in order to mold the resin layer 15. A consecutive molding machine 20 is preferably used which is formed of known extruding sections 21 and 22, which are formed of a hopper, screws 21a and 22a, and the like; a head section 23 for coating and molding the resin layer 15 on the outer peripheral surface of the flexible tube base 14; a cooling section 24; a transport section 25 (a supply drum 28 and a winding drum 29) which transports a linking flexible tube base 31 to the head section 23; and a control unit 26 which controls the above. The head section 23 is preferably formed of a nipple 32, a die 33, and a supporter 34 which securely supports the above. It is possible to use, for example, the apparatus described in FIGS. 3 to 5 of JP2011-72391A as a configuration example of such an apparatus.

An inner section of the die 33 is preferably heated to a predetermined molding temperature. The molding temperature is preferably set to a range of 150° C. to 300° C. It is possible to make each temperature of a soft resin 39 and a hard resin 40 a high temperature by controlling the temperature by heating a heating section inside an apparatus; however, in addition to this, it is possible to further increase the temperature of each of the soft resin 39 and the hard resin 40 as rotation speeds of each of the screws 21a and 22a are increased and it is possible to improve the fluidity of each. At that time, it is possible to adjust each molding thickness of the inner layer 17 and the outer layer 18 by setting a transport speed of the linking flexible tube base 31 to be constant and changing each discharging amount of the soft resin 39 and the hard resin 40 in a melted state.

Description will be given of a process when molding the resin layer 15 on the linking flexible tube base 31 using the consecutive molding machine 20. When the consecutive molding machine 20 performs the molding step, the soft resin 39 and the hard resin 40 in a melted state are extruded from the extruding sections 21 and 22 to the head section 23. Along with this, the transport section 25 is operated to transport the linking flexible tube base 31 to the head section 23. At that time, the extruding sections 21 and 22 are in a state of constantly extruding and supplying the soft resin 39 and the hard resin 40 to the head section 23 and the soft resin 39 and the hard resin 40 which are extruded from the extruding sections 21 and 22 to gates 35 and 36 pass through an edge to merge and pass through a resin path 38 in an overlapped state to be supplied to a molding path 37. Due to this, the resin layer 15 molded with a double layer where the inner layer 17 for which the soft resin 39 is used and the outer layer 18 for which the hard resin 40 is used are overlapped is formed.

The linking flexible tube base 31 is molded by a plurality of the flexible tube bases 14 being linked and the resin layer 15 is consecutively formed with respect to the plurality of the flexible tube bases 14 while being transported inside the molding path 37. When molding the resin layer 15 from the one end 14a side (the front end side) of one flexible tube base to the other end 14b side (the base end side), directly after starting to discharge a resin from the extruding sections 21 and 22, the thickness of the inner layer 17 is set to be thick. Then, the ratio of the thickness of the outer layer 18 is gradually increased in a middle section toward the other end 14b side. Due to this, the discharge amount of the resin is preferably controlled so as to match the incremental thickness ratio of the resin layer 15.

Since a joint member 30 is a linking section of two of the flexible tube bases 14, the control unit 26 is used for switching the discharge amount of the extruding sections 21 and 22. In detail, the control unit 26 preferably switches the discharge amounts of the extruding sections 21 and 22 so as to be from the thickness ratio at the other end 14b side (a base end side) of the one flexible tube base 14 to the thickness ratio at the one end 14a side (a front end side) of the next flexible tube base 14. When molding the resin layer 15 from the one end 14a side of the next flexible tube base 14 to the other end 14b side, the extruding sections 21 and 22 are preferably controlled such that the thickness of the outer layer is gradually increased from one end side to the other end side in the same manner.

After being detached from the consecutive molding machine 20, the joint member 30 is detached from the flexible tube bases 14 and the linking flexible tube base 31 where the resin layer 15 is molded to the rearmost end is separated into each of the flexible tube bases 14. Next, a coating film 16 is coated on the resin layer 15 with respect to the separated flexible tube bases 14 and the flexible tube 3a is completed. The completed flexible tube 3a is transported to the assembling step of an electronic endoscope.

Resin Layer

Embodiment According to First Invention

A resin layer of the present embodiment is configured by at least two layers of a first layer and a second layer, in which the first layer includes one or more elastomers selected from a group consisting of polyester elastomers, polyurethane elastomers, and polyamide elastomers or chain-extended forms thereof. On the other hand, the second layer includes chain-extended forms of two or more elastomers selected from a group consisting of polyester elastomers, polyurethane elastomers, and polyamide elastomers. In other words, the second layer contains elastomer blend chain-extended forms. In detail, it is preferable to have a blend with at least one type selected from polyester elastomers, polyurethane elastomers, and polyamide elastomers.

As described above, the second layer uses a blend of two or more types of elastomers. As the combination of elastomers, polyester elastomers and other elastomers are preferably combined. With regard to the blending ratio, the other elastomers are preferably 5 to 100 parts by mass with respect to 100 parts by mass of the polyester elastomers, more preferably 10 to 80 parts by mass, and particularly preferably 15 to 60 parts by mass.

Preferable combinations are as follows.

| Main elastomers | Sub elastomers |
|---|---|
| PE | PU |
| PE | PA |
| PE | PU + PA |

PE: Polyester elastomers
PU: Polyurethane elastomers
PA: Polyamide elastomers

An elastomer blend may be used for the first layer in the same manner and, as the combination, an aspect where polyurethane elastomers are combined with other elastomers or an aspect where polyamide elastomers are combined with other elastomers is preferable. With regard to the blend, the other elastomers are preferably 5 to 100 parts by mass with respect to 100 parts by mass of polyurethane elastomers or polyamide elastomers, more preferably 10 to 80 parts by mass, and particularly preferably 15 to 60 parts by mass.

Preferable combinations are as follows.

| Main elastomers | Sub elastomers |
| --- | --- |
| PU | PE |
| PU | PA |
| PU | PA, PU |
| PA | PU |
| PA | PE |
| PA | PE, PU |

PE: Polyester elastomers
PU: Polyurethane elastomers
PA: Polyamide elastomers

First Layer

The first layer is preferably the inner layer 17 (FIG. 2). In the present embodiment, the inner layer coats the entire peripheral surface surrounding an axis of the flexible tube base. The first layer may be an elastomer formed of the resin, a chain-extended form thereof, or a mixture which contains an arbitrary additive.

Chain Extender

A chain extending process is preferably carried out by blending a chain extender with the resin elastomers in order to make the chain-extended form. The chain extender may be appropriately selected and a chain extender selected from polyfunctional epoxy compounds, polyfunctional isocyanate compounds, polyfunctional amino compounds, oxazoline compounds, carbodiimide compounds, and acid anhydrides is preferably used. Among these, it is more preferable to use polyfunctional isocyanate compounds, oxazoline compounds, and carbodiimide compounds. By applying these selected chain extenders, it is possible to comprehensively improve the performance of the resin layer which is suitable for the flexible tube and it is possible to improve the performances, in particular, the peracetic acid resistance, elasticity, and bending durability of the obtained flexible tube, which is preferable.

Polyfunctional Epoxy Compounds

The polyfunctional epoxy compound which is used as the chain extender is not particularly limited as long as the compound contains two or more epoxy groups and it is possible to use any monomers, oligomers, or polymers. In a case where the epoxy group-containing compound is a polymer, from the viewpoint of having an excellent effect of improving the heat aging resistance and growth rate, not being easily gelled, and having excellent handleability, the weight average molecular weight is preferably 2,000 to 1,000,000, more preferably 3,000 to 500,000, and even more preferably 4,000 to 250,000.

Examples of the epoxy group-containing compounds include epoxy group-containing (meth)acryl-based polymers, epoxy group-containing polystyrene, epoxidized vegetable oil, polyglycidyl ethers, and the like.

Epoxy group-containing (meth)acryl-based polymers are not particularly limited as long as the main chain is a (meth)acryl-based polymer and two or more epoxy groups are contained in the molecule. Here, in the present invention, (meth)acryl has the meaning of one or both of acryl and methacryl. The (meth)acryl-based polymer as the main chain may be either of a homopolymer and a copolymer. Examples of epoxy group-containing (meth)acryl-based polymers include methyl methacrylate-glycidyl methacrylate copolymers, methyl methacrylate-styrene-glycidyl methacrylate copolymers, and the like. Among these, methyl methacrylate-glycidyl methacrylate copolymers and methyl methacrylate-styrene-glycidyl methacrylate copolymers are preferable.

From the viewpoint of having an excellent effect of improving the heat aging resistance and growth rate, not being easily gelled, and having excellent handleability, the weight average molecular weight of the epoxy group-containing (meth)acryl-based polymers is preferably 3,000 to 300,000 and more preferably 4,000 to 250,000.

The polyglycidyl ethers are not particularly limited as long as two or more glycidyl oxy groups are contained in the molecule. Examples of polyglycidyl ethers include polyglycidyl ether of glycerine epichlorohydrin-0 to 1 mol adduct, polyglycidyl ether of ethylene glycol-epichlorohydrin-0 to 2 mol adduct, polyethylene glycol-diglycidyl ether, neopentyl glycol-diglycidyl ether, trimethylol propane-polyglycidyl ether, and the like.

From the viewpoint of having an excellent effect of improving the heat aging resistance and growth rate and not being easily gelled, the epoxy equivalent of an epoxy group-containing compound is preferably 170 to 10,000 g/equivalent (more narrowly, 170 to 3,300 g/equivalent) and more preferably 200 to 5,000 g/equivalent (more narrowly, 200 to 2,000 g/equivalent).

Examples of commercial products of epoxy group-containing (meth)acryl-based polymers include Joncryl ADR-4368 (acryl-based polymer, powder, weight average molecular weight 6,800, epoxy equivalent 285 g/equivalent, manufactured by BASF Corp.), Marproof G-0150M (acryl-based polymer, powder, weight average molecular weight 8,000 to 10,000, epoxy equivalent 310 g/equivalent, manufactured by NOF Corp.), and Marproof G-2050M (acryl-based polymer, powder, weight average molecular weight 200,000 to 250,000, epoxy equivalent 340 g/equivalent, manufactured by NOF Corp.). Examples of commercial products of epoxy group-containing polystyrene include Marproof G-1010S (styrene-based polymer, powder, weight average molecular weight 100,000, epoxy equivalent 1,700 g/equivalent, manufactured by NOF Corp.). Examples of commercial products of epoxidized vegetable oil include Newsizer 510R (manufactured by NOF Corp.) which is an epoxidized soybean oil, JER1001 manufactured by Mitsubishi Chemical Corp. (solid, epoxy equivalent 450 to 500), JER1010 (solid, epoxy equivalent 3,000 to 5,000), and the like.

Polyfunctional Isocyanate Compounds

Examples of polyfunctional isocyanate compounds include polyfunctional isocyanate compounds which are known in the art such as aromatic, aliphatic, cyclic aliphatic, or alicyclic polyfunctional isocyanate compounds, or mixtures, adducts, modifications, and polymers thereof. In the present invention, among these, polyisocyanate such as tolylene diisocyanate (TDI), 4,4-diphenyl methane diisocyanate (MDI), hydrogenated diphenyl methane diisocyanate (H12 MDI), polyphenyl methane polyisocyanate (Crude MDI), modified-diphenyl methane diisocyanate (modified MDI), xylylene diisocyanate (XDI), hydrogenated xylylene diisocyanate (H-XDI), hexamethylene diisocyanate (HMDI), trimethyl hexamethylene diisocyanate (TMDI), and isophorone diisocyanate (IPDI), or trimeric compounds of these polyisocyanates are preferable.

Carbodiimide Compounds

A carbodiimide compound is a compound which has one or more (two or more is preferable) carbodiimide groups in the molecule. The compound may be an aromatic carbodiimide compound (with 6 to 26 carbon atoms is preferable and with 6 to 18 carbon atoms is more preferable) or may be a non-aromatic carbodiimide compound (with 2 to 24 carbon atoms is preferable and with 2 to 12 carbon atoms is more preferable). Examples of carbodiimide compounds include aromatic and aliphatic carbodiimide compounds. Aliphatic polycarbodiimide compounds which have two or more carbodiimide groups in the molecule are more preferably used and polycarbodiimide which is produced using 4,4'-dicyclohexyl methane diisocyanate is even more preferably used. Examples of polycarbodiimides which are produced using 4,4'-dicyclohexyl methane diisocyanate include "Carbodilite LA-1" and the like manufactured by Nisshinbo Holdings Inc.

Examples of monocarbodiimide compounds, which have one carbodiimide group in the molecule, which are included in the carbodiimide compounds described above include dicyclohexyl carbodiimide, diisopropyl carbodiimide, dimethyl carbodiimide, diisobutyl carbodiimide, dioctyl carbodiimide, t-butyl isopropyl carbodiimide, diphenyl carbodiimide, di-t-butyl carbodiimide, di-β-naphthyl carbodiimide, and the like and among these, in particular, dicyclohexyl carbodiimide or diisopropyl carbodiimide is favorable from the point of being easily obtained industrially.

The number average molecular weight (Mn) of carbodiimide compounds which are used in the present invention is preferably in a range of 100 to 40,000 and more preferably in a range of 100 to 30,000.

Polyfunctional Amino Compounds

Polyfunctional amino compounds may be aromatic amino compounds (with 6 to 26 carbon atoms is preferable and with 6 to 18 carbon atoms is more preferable) or may be non-aromatic amino compounds (with 2 to 24 carbon atoms is preferable and with 2 to 12 carbon atoms is more preferable). Aromatic amines such as m-phenylene diamine, p-phenylene diamine, and 1,3,5-triamino benzene, aliphatic amines such as ethylene diamine, piperazine, and amino methyl piperazine, and amino polymers such as polymers where polyepihalohydrin is modified by the monomer amines described above are preferable.

Polyfunctional Oxazoline

A polyfunctional oxazoline compound is a compound which contains two or more oxazoline groups in the molecule. The compound may be an aromatic polyfunctional oxazoline compound (with 6 to 26 carbon atoms is preferable and with 6 to 18 carbon atoms is more preferable) or may be a non-aromatic polyfunctional oxazoline compound (with 2 to 24 carbon atoms is preferable and with 2 to 12 carbon atoms is more preferable). These are not limited; however, in detail, examples thereof include 2,2'-bis(2-oxazoline), 2,2'-bis(4-methyl-2-oxazoline), 2,2'-bis(4,4'-dimethyl-2-oxazoline), 2,2'-bis(4-ethyl-2-oxazoline), 2,2'-bis(4,4'-diethyl-2-oxazoline), 2,2'-bis(4-propyl-2-oxazoline), 2,2'-bis(4-butyl-2-oxazoline), 2,2'-bis(4-hexyl-2-oxazoline), 2,2'-bis(4-phenyl-2-oxazoline), 2,2'-bis(4-cyclohexyl-2-oxazoline), 2,2'-bis(4-benzyl-2-oxazoline), 2,2'-p-phenylenebis(2-oxazoline), 2,2'-m-phenylenebis(2-oxazoline), 2,2'-o-phenylenebis(2-oxazoline), 2,2'-p-phenylenebis(4-methyl-2-oxazoline), 2,2'-p-phenylenebis(4,4'-dimethyl-2-oxazoline), 2,2'-m-phenylenebis(4-methyl-2-oxazoline), 2,2'-m-phenylenebis(4,4'-dimethyl-2-oxazoline), 2,2'-ethylenebis(2-oxazoline), 2,2'-tetramethylenebis(2-oxazoline), 2,2'-hexamethylenebis(2-oxazoline), 2,2'-octamethylenebis(2-oxazoline), 2,2'-decamethylenebis(2-oxazoline), 2,2'-ethylenebis(4-methyl-2-oxazoline), 2,2'-tetramethylenebis(4,4'-dimethyl-2-oxazoline), 2,2'-9,9'-diphenoxyethanebis(2-oxazoline), 2,2'-cyclohexylenebis(2-oxazoline), 2,2'-diphenylenebis(2-oxazoline), Epocros manufactured by Nippon Shokubai Co., Ltd., and the like. Furthermore, examples include polyoxazoline compounds which include the compounds described above as a monomer unit and the like, for example, styrene 2-isopropenyl-2-oxazoline copolymers and the like. From the viewpoint of reactivity with a polyester carboxy terminal group, Epocros, which is manufactured by Nippon Shokubai Co., Ltd. and has three or more oxazoline groups, is preferable.

Acid Anhydrides

The acid anhydride is preferably a carbon acid anhydride. The acid anhydride may be an aromatic acid anhydride (with 6 to 26 carbon atoms is preferable and with 6 to 18 carbon atoms is more preferable) or may be a non-aromatic acid anhydride (with 2 to 24 carbon atoms is preferable and with 2 to 12 carbon atoms is more preferable). Specific examples of acid anhydrides include anhydrous tetrahydrophthalic acid, alkylated anhydrous tetrahydrophthalic acid, anhydrous hexahydrophthalic acid, alkylated anhydrous hexahydrophthalic acid, succinic anhydride, and maleic anhydride.

The blending amount of the chain extender is preferably 0.01 parts by mass or more of the chain extender with respect to 100 parts by mass of the elastomers (the total in a case of blending), more preferably 0.05 parts by mass or more, and particularly preferably 0.1 parts by mass or more. The upper limit is preferably 10 parts by mass or less, more preferably 5.0 parts by mass or less, and particularly preferably 1.0 part by mass or less. By setting the upper limit to the value described above or less, it is possible to improve the flexibility and bending durability of the obtained flexible tube, which is preferable. By setting the lower limit to the value described above or higher, it is possible to improve the peracetic acid resistance of the obtained flexible tube, which is preferable.

In the present invention, it is possible to use the chain extenders individually or by combining two or more types.

The chain extender preferably configures soft segments which link hard segments formed by elastomers and which have a suitable chain length. From the viewpoint, the blending amount or molecular weight described above are preferably adjusted. The molecular weight of a chain extender is preferably 100 to 50,000, more preferably 120 to 30,000, particularly preferably 150 to 20,000. Here, with regard to the molecular weight of the chain extender of commercial compounds, it is possible to apply a molecular weight which is calculated from a chemical structure described in a catalogue. In a case where a chemical structure is not clear, it is possible to apply a method for determining a molecular weight by a mass spectrometry after carrying out column separation by LC-MS. In addition, in a case where the molecular weight is large and mass spectrometry analysis is difficult, it is possible to measure the weight average molecular weight of polystyrene conversion using GPC. At that time, a GPC apparatus HLC-8220 (manufactured by Tosoh Corp.) is used, THF (tetrahydrofuran) (manufactured by Shonanwako Co., Ltd.) is used as an eluent, G3000HXL+G2000HXL are used for columns, the flow rate is 1 mL/min at 23° C., and detection is carried out by RI.

The chain extending process is preferably performed by melt-kneading a resin mixture which contains elastomers and a chain extender. For the melt-kneading process, there are methods where the process is performed by carrying out the molding using the molding machine after kneading using a kneading machine (an extruder) to set a pellet state in advance or using a hopper, a screw, or the like of the consecutive molding machine; however, a kneading machine is preferably used since it is possible to evenly and equally apply the chain extender. At that time, heating is preferably carried out and it is possible to perform the heating by controlling the temperature of each section of the kneading machine or the consecutive molding machine as above. The set temperature is as described above; however, with regard to the temperature of the resin, heating is preferably carried out to 150° C. to 300° C. and heating is more preferably carried out to 180° C. to 250° C. In this manner, with regard to the elastomers of the present embodiment, the chain extending process is preferably performed in a series of processes of heating, melting, kneading, and extruding at the time of extruding and molding.

Catalyst

The chain extending process of the elastomers is preferably performed by adding a catalyst in addition to the chain extender. The catalyst is preferably at least one selected from amine compounds and tin chelate.

The blending amount of the catalyst is preferably 0.01 parts by mass or more of a catalyst with respect to 100 parts by mass of the elastomers (the total in a case of blending), more preferably 0.02 parts by mass or more, and particularly preferably 0.03 parts by mass or more. The upper limit is preferably 3 parts by mass or less, more preferably 1 part by mass or less, and particularly preferably 0.5 parts by mass or less. By setting the upper limit to the value described above or less, it is possible to suppress heat deterioration of a polymer due to an excess of the catalyst, which is preferable. By setting the lower limit to the value described above or higher, it is possible to improve the peracetic acid resistance of the obtained flexible tube, which is preferable.

The first layer described above preferably further contains a heating stabilizer which is selected from a phenol-based compound, an amine-based compound, a phosphorus-based compound, a sulfur-based compound, and a phenylacrylate-based compound. Among these, an amine-based compound is preferable and in particular, a hindered amine-based compound is particularly preferable. Due to this, it is possible to suppress changes in the quality of a resin due to the heating history during the kneading or molding process and it is possible to stabilize the operability of the device during diagnosis by a physician.

The blending amount of the heating stabilizer is preferably 0.01 parts by mass or more of the heating stabilizer with respect to 100 parts by mass of the elastomers (the total in a case of blending), more preferably 0.1 parts by mass or more, and particularly preferably 0.5 parts by mass or more. The upper limit is preferably 10 parts by mass or less, more preferably 5 parts by mass or less, and particularly preferably 3 parts by mass or less. By setting the upper limit to the value described above or less, it is possible to suppress bleeding out of the heating stabilizer from the surface of the obtained flexible tube and to exhibit high top coat adhesion, which is preferable. By setting the lower limit to the value described above or more, it is possible to improve the peracetic acid resistance of the obtained flexible tube, which is preferable.

Second Layer

The second layer is preferably the outer layer 18 (FIG. 2). In the present embodiment, the outer layer is in contact with the first layer and forms an outer layer which coats the entire peripheral surface surrounding the axis of the first layer. With regard to the second layer, without applying the elastomers themselves, a mixture which contains the chain-extended forms thereof or other components thereof is applied. In this manner, applying chain-extended forms of specific elastomers to the second layer (preferably the outer layer) is one of the features of the present embodiment and due to this, remarkable effects are exhibited when setting a laminated resin of a flexible tube for an endoscope.

The types and amount of the chain extender, the form of the chain extending process, the types and amount of the catalyst, and the types and amount of the heating stabilizer are all the same as described in the first layer.

Physical Properties

The molecular weight of the elastomers which are applied to the first layer and the second layer is not particularly limited, however, from the viewpoint of configuring favorable hard segments and drawing out a favorable interaction with soft segments formed by the chain extender, a molecular weight of 10,000 to 1,000,000 is preferable, a molecular weight of 20,000 to 500,000 is more preferable, and a molecular weight of 30,000 to 300,000 is particularly preferable.

In the present specification, the molecular weight of the polymer compounds which include elastomers has the meaning of the weight average molecular weight unless otherwise stated. It is possible to measure the weight average molecular weight as a molecular weight of polystyrene conversion by GPC. At that time, a GPC apparatus HLC-8220 (manufactured by Tosoh Corp.) is used and an eluent is selected by appropriately matching with the polymer compounds. Chloroform is used in a case of polyester elastomers, NMP (N-methyl-2-pyrrolidone) is used in a case of polyurethane elastomers, and m-cresol/chloroform (manufactured by Shonanwako Co., Ltd.) is used in a case of polyamide elastomers, G3000HXL+G2000HXL are used for the columns, the flow rate is 1 mL/min at 23° C., and detection is carried out by RI.

The physical properties of the elastomers and the chain-extended forms thereof which configure the first layer (an inner layer) are preferably favorably set. For example, A hardness: JIS K 7215 is preferably 40 or more, more preferably 50 or more, and particularly preferably 60 or more. 98 or less is preferable, 95 or less is more preferable, and 90 or less is particularly preferable.

A storage elastic modulus E' is preferably 1 MPa or more, more preferably 2 MPa or more, and particularly preferably 3 MPa or more. 150 MPa or less is preferable, 100 MPa or less is more preferable, and 50 MPa or less is particularly preferable. A loss elastic modulus E" is preferably 0.1 MPa or more, more preferably 0.3 MPa or more, and particularly preferably 0.5 MPa or more. 20 MPa or less is preferable, 10 MPa or less is more preferable, and 5 MPa or less is particularly preferable. A loss tangent is preferably 0.01 or more, more preferably 0.03 or more, and particularly preferably 0.05 or more. 1 or less is preferable, 0.5 or less is more preferable, and 0.3 or less is particularly preferable.

Here, in the present specification, the value related to viscoelasticity is a value of 25° C. unless otherwise stated. The measuring method conforms to JIS-K7244-4.

The physical properties of the chain-extended forms of the elastomers which configure the second layer (an outer layer) are preferably favorably set. For example, D hardness: JIS K 7215 is preferably 20 or more, more preferably 25 or more, and particularly preferably 30 or more. 80 or less is preferable, 70 or less is more preferable, and 60 or less is particularly preferable.

The storage elastic modulus E' is preferably 1 MPa or more, more preferably 5 MPa or more, and particularly preferably 10 MPa or more. 1 GPa or less is preferable, 500 MPa or less is more preferable, and 300 MPa or less is particularly preferable. The loss elastic modulus E" is preferably 0.1 MPa or more, more preferably 0.5 MPa or more, and particularly preferably 1 MPa or more. 100 MPa or less is preferable, 50 MPa or less is more preferable, and 30 MPa or less is particularly preferable. The loss tangent is preferably 0.01 or more, more preferably 0.03 or more, and particularly preferably 0.05 or more. 1 or less is preferable, 0.5 or less is more preferable, and 0.3 or less is particularly preferable.

A 100% modulus value of the first layer is preferably 0.5 MPa or more, more preferably 1.0 MPa or more, and particularly preferably 1.5 MPa or more. 20 MPa or less is preferable, 15 MPa or less is more preferable, and 10 MPa or less is particularly preferable.

A 100% modulus value of the second layer is preferably 1.0 MPa or more, more preferably 1.5 MPa or more, and particularly preferably 2.0 MPa or more. 30 MPa or less is preferable, 25 MPa or less is more preferable, and 20 MPa or less is particularly preferable.

Here, the modulus value in the present specification is a value of 25° C. unless otherwise stated. The measuring method conforms to JIS-K7311.

The resin layer is preferably soluble in 1,1,1,3,3,3-hexafluoro-2-propanol (specific solvent). Being soluble in a specific solvent has the meaning of exhibiting solubility of 5 mass % at 20° C. In this manner, being soluble in a specific solvent has the technical meaning that the resin does not have a three-dimensional (cross-linked) structure and exhibits flexibility as the resin layer of a flexible tube for an endoscope, which is preferable.

The elastomers of the resin layer are preferably substantially not cross-linked. Here, substantially not cross-linked refers to not having a branch structure in a range in which it is possible to detect the resin using NMR or the like in addition to being not cross-linked.

By the elastomers of the resin layer (particularly the second layer, the layer A, and the outer layer) according to the present embodiment being substantially not cross-linked, preferable flexibility and bending durability performances as a resin layer of a flexible tube for an endoscope are exhibited.

Resin Layer

Embodiment According to Second Invention

A resin layer of a flexible tube of the present embodiment is preferably formed of a single layer or multiple layers and the outermost layer of the resin layer is preferably formed of a layer A (a layer which contains polyester elastomers, and, hindered phenol compounds or hindered amine compounds). Here, "outermost layer" of the resin layer has the meaning of the resin layer in a case where the resin layer is a one layer structure and the resin layer on the uppermost layer side out of the resin layers of the flexible tube in a case of a multiple layer structure of two or more layers. However, an outside layer (such as a top coat) may be further provided in a range in which the effects of the present invention are exhibited.

The hindered phenol compound described above is preferably a compound which has a structure site which is represented by the following Formula (1) and the hindered amine compound described above is preferably a compound which has a structure site which is represented by the following Formula (2).

Formula (1)

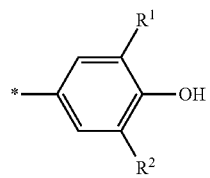

(1)

-continued

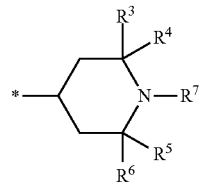

(2)

In Formula (1) described above, $R^1$ and $R^2$ are a hydrogen atom, an alkyl group having 1 to 12 carbon atoms (preferably an alkyl group having 1 to 8 carbon atoms, for example, a methyl group, an ethyl group, an n-butyl group, an isopropyl group, a sec-butyl group, a t-butyl group, a t-pentyl group, a t-hexyl group, or a t-octyl group), or an aralkyl group having 7 to 36 carbon atoms (preferably 7 to 30). At least one of $R^1$ and $R^2$ is preferably a secondary alkyl group or a tertiary alkyl group and at least one of $R^1$ and $R^2$ is more preferably a tertiary alkyl group. In addition, both $R^1$ and $R^2$ are also preferably tertiary alkyl groups (preferably t-butyl groups).

In Formula (1), * represents a bonding site.

A compound which has a structure site which is represented by Formula (1) described above is preferably a compound which is represented by the following Formula (1-1) or (1-2).

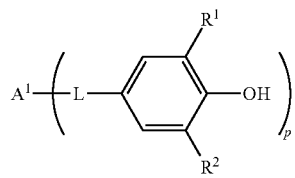

(1-1)

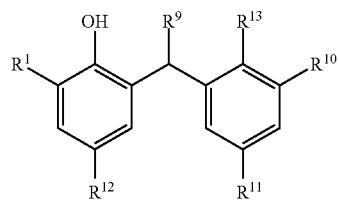

(1-2)

In the formula, $R^1$ and $R^2$ respectively have the same meaning as $R^1$ and $R^2$ in Formula (1).

L indicates a single bond or a divalent linking group. L is preferably an alkylene group having 1 to 10 carbon atoms (preferably 1 to 5 carbon atoms), an alkenylene group having 2 to 10 carbon atoms (preferably 2 to 5 carbon atoms), or a group which is represented by -$L^1$-C(=O)—O-$L^2$-. Here, $L^1$ and $L^2$ indicate a single bond, an alkylene group having 1 to 10 carbon atoms (preferably 1 to 5 carbon atoms), a carbonyl group, an oxygen atom, or a combination thereof.

p is an integer of 2 to 4 and $A^1$ indicates a divalent to tetravalent linking group. $A^1$ is preferably a divalent to tetravalent organic group, the organic group preferably has 1 to 20 carbon atoms, more preferably 1 to 15, even more preferably 1 to 12, and especially preferably 1 to 10.

In a case where p is 2 and $A^1$ is a divalent organic group, $A^1$ is preferably a divalent aliphatic group (preferably an alkylene group) with 1 to 10 carbon atoms (preferably 1 to 5 carbon atoms) or an arylene group having 6 to 22 carbon atoms (preferably 6 to 14 carbon atoms).

In a case where p is 3 and $A^1$ is a trivalent linking group, $A^1$ is preferably a group which is represented by the following Formula (A). In the following Formula (A), * indicates a linking site.

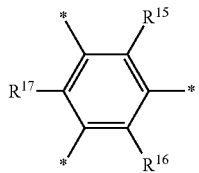

(A)

In Formula (A) described above, * indicates a bonding site. $R^{15}$ to $R^{17}$ indicate a hydrogen atom or an alkyl group having 1 to 10 carbon atoms (preferably 1 to 6 carbon atoms and more preferably 1 to 3 carbon atoms).

In a case where p is 4 and $A^1$ is a tetravalent linking group, $A^1$ is preferably a quaternary carbon atom. In this case, a linking group L is preferably a group which is represented by -$L^1$-C(=O)—O-$L^2$-. Here, $L^1$ and $L^2$ respectively have the same meaning as $L^1$ and $L^2$ described above.

$R^9$ to $R^{12}$ have the same meaning as $R^1$. $R^{13}$ is a reactive organic substituent group, preferably a vinyl group-containing group, and more preferably a (meth)acryloyl group-containing group.

Formula (2)

In Formula (2) described above, $R^3$ to $R^6$ indicate a hydrogen atom or an alkyl group having 1 to 12 carbon atoms (preferably 1 to 8 carbon atoms and more preferably 1 to 5 carbon atoms). Examples of $R^3$ to $R^6$ include a methyl group, an ethyl group, an n-butyl group, an isopropyl group, a sec-butyl group, a t-butyl group, a t-pentyl group, a t-hexyl group, a t-octyl group, and the like. $R^3$ to $R^6$ are preferably a primary (straight-chain) alkyl group and all $R^3$ to $R^6$ are more preferably primary alkyl groups (particularly preferably methyl groups).

In Formula (2), $R^7$ indicates a hydrogen atom, an alkyl group having 1 to 18 carbon atoms (preferably 1 to 10 carbon atoms, more preferably 1 to 5 carbon atoms, even more preferably 1 to 3 carbon atoms, and especially preferably 1 or 2 carbon atoms), or —$OR^8$, and $R^8$ indicates a hydrogen atom or an alkyl group having 1 to 20 carbon atoms (preferably 1 to 12 carbon atoms). $R^7$ is preferably a hydrogen atom among these since a higher chemical resistance is exhibited.

In Formula (2) described above, * represents a bonding site.

A compound which has a structure site which is represented by Formula (2) described above is preferably a compound which is represented by the following Formula (2-1) or a compound which has a repeating unit which is represented by Formula (2-2).

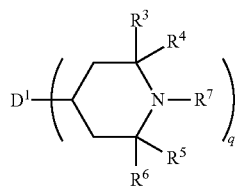

(2-1)

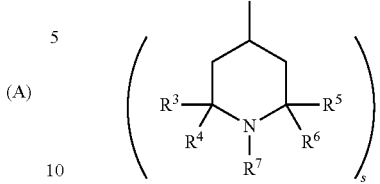

(2-2)

In the formula, $R^3$ to $R^7$ respectively have the same meaning as $R^3$ to $R^7$ in Formula (2) described above and the preferable ranges are also the same. q indicates an integer of 2 or greater and $D^1$ indicates a divalent or higher linking group. s represents 1 or 2. r represents an integer, and the range of the polymerization degree value which will be described below is preferable. Q represents an (s+2)-valent linking group and examples thereof include a group which includes an imino group ($NR^N$), a group which includes a triazine linking group, and the like. Examples of $R^N$ include a hydrogen atom, an alkyl group having 1 to 6 carbon atoms, and a pyridyl group-containing group which is represented by Formula (2).

A compound which has a structure site which is represented by Formula (2) described above is more preferably a compound which is represented by the following formulas (2-A) to (2-C) or (2-G) or a polymer or oligomer which has a repeating unit which is represented by the following Formula (2-D) (preferably a polymer or oligomer which has any repeating unit of formulas (2D1) to (2D3)).

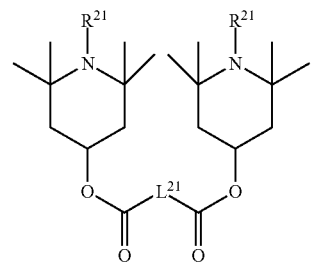

(2-A)

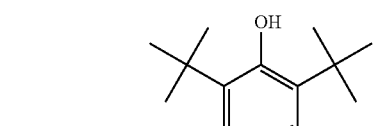

(2-B)

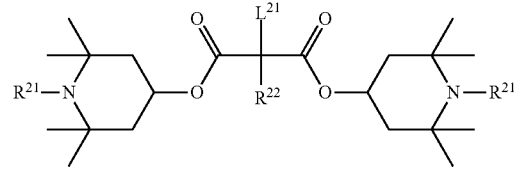

(2-C)

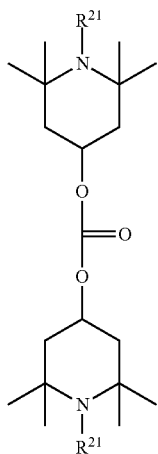

(2-D)

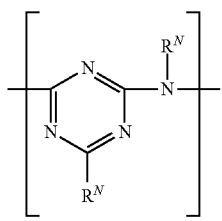

(2-E)

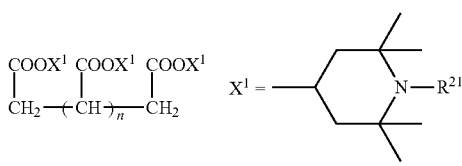

(2D1)

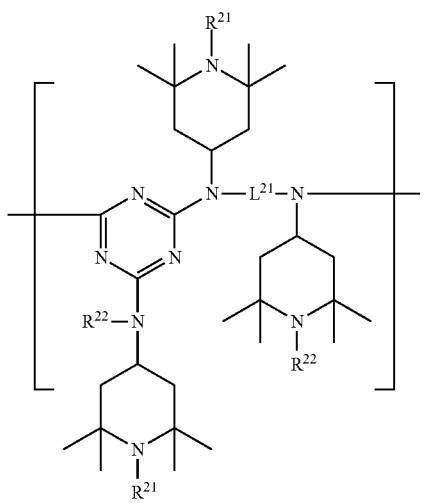

(2D2)

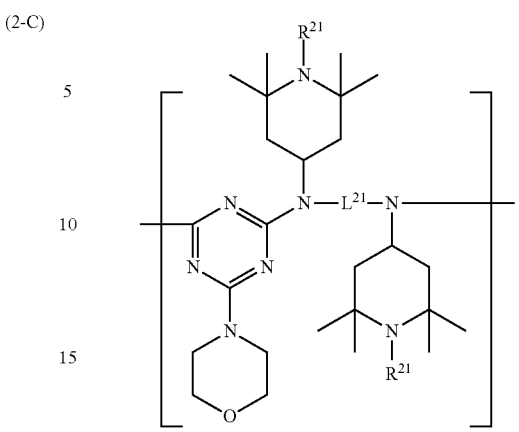

(2D3)

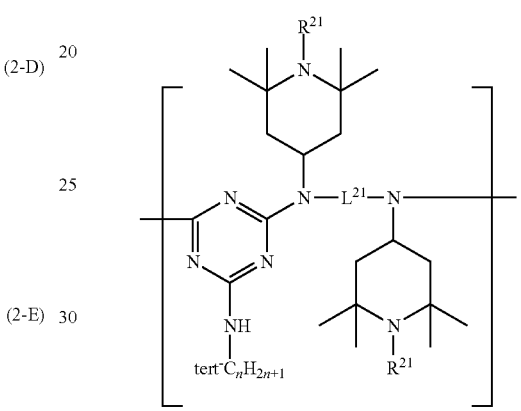

$R^{21}$ in each of the formulas described above has the same meaning as $R^7$ in Formula (2) and preferable forms thereof are the same.

$R^{22}$ indicates a hydrogen atom or an alkyl group having 1 to 20 carbon atoms (preferably 1 to 12 carbon atoms, more preferably 1 to 8 carbon atoms, and even more preferably 1 to 6 carbon atoms). $L^{21}$ indicates a single bond or an alkylene group having 1 to 20 carbon atoms (preferably 1 to 10 carbon atoms). $R^N$ has the same meaning as Formula (2-2). n indicates an integer of 1 to 20 (preferably 1 to 10).

In a case where a compound which has a structure site which is represented by Formula (2) described above is a polymer or oligomer, the number of the repeating units (polymerization degree) is preferably 2 to 100, more preferably 2 to 50, and even more preferably 2 to 10. In addition, the terminal structure of the polymer or oligomer is not particularly limited, however, for example, it is possible for the structure to be a hydrogen atom, a substituted or unsubstituted amino group, a substituted or unsubstituted triazil group.

In the resin components which configure the layer A of the resin layer (preferably an outermost layer), the content of polyester elastomers is preferably 50 mass % or more, more preferably 55 mass % or more, even more preferably 60 mass % or more, and especially preferably 65 mass % or more. In addition, the content of the polyester elastomers in the resin components which configure the layer A may be 100 mass %; however, 90 mass % or less is preferable, 80 mass % or less is more preferable, and 75 mass % or less is even more preferable. By setting the content of polyester elastomers in the layer A within the preferable range described above and blending a soft resin in the remainder, it is possible to impart superior flexibility.

When the layer A of the resin layer includes components other than polyester elastomers as the resin components, at least one type of polyurethane elastomers and polyamide elastomers as a softer resin is preferably included in the remainder apart from the polyester elastomers in the resin components and at least polyurethane elastomers are preferably included. In the resin components of the layer A of the resin layer, the content of polyurethane elastomers is preferably 5 mass % or more, more preferably 10 mass % or more, even more preferably 15 mass % or more, especially preferably 20 mass % or more, and most preferably 25 mass % or more. In addition, the content of polyurethane elastomers in the resin components of the layer A of the resin layer is preferably 50 mass % or less, more preferably 40 mass % or less, and even more preferably 35 mass % or less.

In addition, in a more preferable embodiment of the present invention, the layer A of the resin layer is preferably used for an outermost layer of the resin layer, and preferably contains both hindered phenol compounds and hindered amine compounds. By hindered phenol compounds and hindered amine compounds being present together in the layer A of the resin layer, the resistance with respect to a disinfectant is synergistically improved compared to a case where each is contained individually.

In a preferable aspect of the layer A of the resin layer, 0.01 parts by mass or more of the hindered phenol compounds described above are contained with respect to 100 parts by mass of the resin components in the layer A of the resin layer and more preferably 0.1 parts by mass or more are contained. As the upper limit side, 7 parts by mass or less are preferably contained and 5 parts by mass or less are more preferably contained. 0.01 parts by mass or more of the hindered amine compounds described above are preferably contained with respect to 100 parts by mass of the resin components and 0.1 parts by mass or more are more preferably contained. As the upper limit side, 7 parts by mass or less are preferably contained and 5 parts by mass or less are more preferably contained. In the layer A of the resin layer, the total amount of the hindered phenol compounds described above and the hindered amine compounds described above is preferably 7 parts by mass or less with respect to 100 parts by mass of the resin components in the layer A of the resin layer and more preferably 6 parts by mass or less. As the lower limit side, 0.01 parts by mass or more are preferably contained and 0.1 parts by mass or more are more preferably contained.

In a case where the resin layer is formed of multiple layers, at least one layer other than the layer A (preferably an outermost layer) preferably contains polyurethane elastomers or polyamide elastomers (this layer is referred to below as a "layer B"). The layer B preferably contains at least polyurethane elastomers. The layer B preferably has polyurethane elastomers as a main component and, in this case, the content of polyurethane elastomers is preferably 50 mass % or more in the resin components of the layer B, more preferably 70 mass % or more, even more preferably 80 mass % or more, and especially preferably 90 mass % or more. All the resin components in the layer B are also preferably polyurethane elastomers; however, if not, the remainder is preferably configured by polyamide elastomers and/or polyester elastomers.

In addition, the layer B may have polyamide elastomers as a main component. For example, the content of polyamide elastomers in the layer B which contains polyamide elastomers may be 50 mass % or more in the resin components and 70 mass % or more is also possible. It is also possible that all the resin components in the layer B are polyamide elastomers; however, if not, the remainder is preferably configured by polyurethane elastomers and/or polyester elastomers and being configured by polyurethane elastomers is more preferable.

When being used as an outermost layer, the layer B described above preferably includes at least one type of hindered phenol compound and hindered amine compound. Due to this, it is possible to further improve the chemical resistance of a flexible tube. In a case of using the layer B for an inner layer, there are cases where these are preferably not included in consideration of adhesion and the like with an outer layer rather than chemical resistance. In a case of using the layer B for the outermost layer, the preferable blending amount of the hindered phenol compounds and the hindered amine compounds is the same as for the layer A.

The flexible tube of the present invention is preferably provided with a resin layer with a double layer structure formed of an inner layer and an outer layer. In this case, the inner layer is configured by the layer B of the resin layer described above and the outer layer is configured by the layer A of the resin layer described above. The blend of each of the resin layers is preferably as follows. In the present invention, it is also preferable to have a set of resin compositions formed by the A layer and B layer described above. Here, the technical term "resin composition" is used with the meaning that the resin itself is included.

TABLE S-1

In a case of prioritizing the adhesion of an inner layer and an outer layer

|  |  | Elastomers | Additives |
|---|---|---|---|
| Inner layer | B layer | PU (PE, PA) |  |
| Outer layer | A layer | PE (PU, PA) | HA, HP |

TABLE S-2

In a case of prioritizing the chemical resistance

|  |  | Elastomers | Additives |
|---|---|---|---|
| Inner layer | B layer | PU (PE, PA) | HA, HP |
| Outer layer | A layer | PE (PU, PA) | HA, HP |

PE: Polyester elastomers
PU: Polyurethane elastomers
PA: Polyamide elastomers
HA: Hindered amine
HP: Hindered phenol
( ) is an arbitrary element Physical Properties The molecular amount of the applied elastomers is not particularly limited; however, a molecular weight of 10,000 to 1,000,000 is preferable, a molecular amount of 20,000 to 500,000 is more preferable, and a molecular weight of 30,000 to 300,000 is particularly preferable.

The physical properties of the layer B described above (preferably an inner layer) are preferably favorably set. For example, A hardness: JIS-K7215 is preferably 40 or more, more preferably 50 or more, and particularly preferably 60 or more. The range on the upper limit side is preferably 98 or less, more preferably 95 or less, and particularly preferably 90 or less.

The storage elastic modulus E' of the layer B described above is preferably 1 MPa or more, more preferably 2 MPa or more, and particularly preferably 3 MPa or more. The range on the upper limit side is preferably 150 MPa or less, more preferably 100 MPa or less, and particularly preferably 50 MPa or less. The loss elastic modulus E" of the layer B described above is preferably 0.1 MPa or more, more preferably 0.3 MPa or more, and particularly preferably 0.5 MPa or more. The range on the upper limit side is preferably 20 MPa or less, more preferably 10 MPa or less, and particularly preferably 5 MPa or less. The loss tangent of the layer B described above is preferably 0.01 or more, more preferably 0.03 or more, and particularly preferably 0.05 or more. The range on the upper limit side is preferably 1 or less, more preferably 0.5 or less, and particularly preferably 0.3 or less.

The physical properties of the layer A of the resin layer are preferably favorably set. For example, D hardness: JIS-K7215 is preferably 20 or more, more preferably 25 or more, and particularly preferably 30 or more. The range on the upper limit side is preferably 80 or less, more preferably 70 or less, and particularly preferably 60 or less.

The storage elastic modulus E' of the layer A of the resin layer is preferably 1 MPa or more, more preferably 5 MPa or more, and particularly preferably 10 MPa or more. The range on the upper limit side is preferably 1 GPa or less, more preferably 500 MPa or less, and particularly preferably 300 MPa or less. The loss elastic modulus E" of the layer A of the resin layer is preferably 0.1 MPa or more, more preferably 0.5 MPa or more, and particularly preferably 1 MPa or more. The range on the upper limit side is preferably 100 MPa or less, more preferably 50 MPa or less, and particularly preferably 30 MPa or less. The loss tangent of the layer A of the resin layer is preferably 0.01 or more, more preferably 0.03 or more, and particularly preferably 0.05 or more. The range on the upper limit side is preferably 1 or less, more preferably 0.5 or less, and particularly preferably 0.3 or less.

A 100% modulus value of the layer B described above is preferably 0.5 MPa or more, more preferably 1.0 MPa or more, and particularly preferably 1.5 MPa or more. A range on the upper limit side is preferably 20 MPa or less, more preferably 15 MPa or less, and particularly preferably 10 MPa or less.

A 100% modulus value of the layer A of the resin layer is preferably 1.0 MPa or more, more preferably 1.5 MPa or more, and particularly preferably 2.0 MPa or more. The range on the upper limit side is preferably 30 MPa or less, more preferably 25 MPa or less, and particularly preferably 20 MPa or less.

Here, a modulus value in the present specification is a value of 25° C. unless otherwise stated. The measuring method conforms to JIS-K7311.

Top Coat

The top coat (a coat layer) 16 is applied to the flexible tube for an endoscope of the present embodiment. The materials for the top coat are not particularly limited; however, urethane coating materials, acryl coating materials, fluorine coating materials, silicon coating materials, epoxy coating materials, polyester coating materials, and the like are applied. From the viewpoint that the adhesion to the resin layer is remarkable and the chemical resistance is excellent, which are advantages of the present embodiment, urethane coating materials, acryl coating materials, and fluorine coating materials are preferable. The film-coating of the top coat layer may use a normal method; however, examples thereof include a form of curing by including a curing agent as necessary in a solution where the coating components described above are dissolved in a predetermined solvent. Examples of the curing process include heating at 100° C. to 200° C. and the like.

The main purpose of using a top coat in the present embodiment is to protect or polish the flexible tube surface, impart a sliding property, and impart chemical resistance. Therefore, the top coat preferably has a high elastic modulus, a smooth surface, and excellent chemical resistance. The storage elastic modulus E' in the top coat single layer is preferably 1 MPa or more, more preferably 5 MPa or more, and particularly preferably 10 MPa or more. 1 GPa or less is preferable, 500 MPa or less is more preferable, and 300 MPa or less is particularly preferable. By setting the storage elastic modulus E' to 1 MPa or more, it is possible to exhibit a surface protection function as a top coat and, moreover, by setting the storage elastic modulus E' to 1 GPa or less, it is possible to maintain the flexibility of the obtained flexible tube.

In the embodiment described above, a resin layer molded with a double layer is formed by placing a soft resin layer (a first layer and the layer B) as an inner layer and a hard resin layer (a second layer and the layer A) as an outer layer; however, the hard resin layer may be placed as an inner layer and a soft resin layer may be placed as an outer layer. In the embodiment described above, description is given with an outer skin layer with a double layer configuration as an example; however, the outer skin layer may have a multiple layer configuration of two or more layers. Both layers need not be laminated in contact with each other and other functional layers may be interposed therebetween.

In the embodiment described above, description is given with an electronic endoscope which observes an image in which the state of a subject is imaged using an imaging apparatus as an example; however, the present invention is not limited thereto and is able to be applied to an endoscope which observes the state of a subject by employing an optical image guide.

It is possible to widely apply the flexible tube according to the present invention with respect to endoscope type medical devices without being limited to being used in an endoscope. For example, it is also possible to apply the present invention to an endoscope, a front end of which is equipped with a clip or a wire, or equipment which is equipped with a basket or a brush, and excellent effects are exhibited. Here, the endoscope type medical device has a meaning that widely includes medical and clinical equipment which has flexibility and is used by being inserted into a body such as remote controlled type medical devices in addition to medical devices which have the endoscope described above as a basic structure.

EXAMPLES

Description will be given below of the present invention in more detail through examples; however, the present invention is not to be interpreted as being limited due to this. Here, the symbols and the like of blending components are in common in Examples I and II; however, these are distinguished in each of the Examples.

Example I

Example According to First Invention

Resin mixtures described in Tables I-1 and I-2 below were prepared, a melt-kneading process was performed at a screw rotation speed of 100 rpm at a barrel setting temperature of 210° C. using a double axis kneading machine manufactured by Technovel Corp. (product name: KZW15-30MG), discharged resin strands in melted state were cooled in a water tank, and then samples in pellet form were manufactured by a pelletizer. The tests described at the end were performed on the produced elastic material samples. The results are shown in Table I-3.

TABLE I-1-1

Resin for second layer (outer layer)

|  |  | A-1 | A-2 | A-3 | A-4 | A-5 | A-6 | A-7 | A-8 | A-9 | A-10 |
|---|---|---|---|---|---|---|---|---|---|---|---|
| Elastomers | PE1 | 80 |  |  |  | 70 | 80 | 80 | 80 | 80 | 80 |
|  | PE2 |  | 60 |  | 75 |  |  |  |  |  |  |
|  | PE3 |  |  | 50 |  |  |  |  |  |  |  |
|  | PU1 |  | 40 | 50 |  |  |  |  |  |  |  |
|  | PU2 | 20 |  |  |  |  |  | 20 | 20 | 20 | 20 |
|  | PU3 |  |  |  | 15 |  |  |  |  |  |  |
|  | PA1 |  |  |  | 15 | 30 |  |  |  |  |  |
| Chain extender | PBO | 0.5 | 0.5 | 0.5 | 0.5 | 0.5 |  |  |  |  |  |
|  | LA-1 |  |  |  |  |  | 0.5 |  |  |  |  |
|  | SBXL P |  |  |  |  |  |  | 0.5 |  |  |  |
|  | HMDI |  |  |  |  |  |  |  | 0.5 |  |  |
|  | TPA-100 |  |  |  |  |  |  |  |  | 0.5 |  |
|  | JER1010 |  |  |  |  |  |  |  |  |  | 0.5 |
|  | MA |  |  |  |  |  |  |  |  |  |  |
| Catalyst | DABCO | 0.05 | 0.05 | 0.05 | 0.05 | 0.05 | 0.05 | 0.05 | 0.05 | 0.05 | 0.05 |
|  | DBTDL |  |  |  |  |  |  |  |  |  |  |
| Heating stabilizer | TIN770 | 1.0 | 1.0 | 1.0 | 1.0 | 1.0 | 1.0 | 1.0 | 1.0 | 1.0 | 1.0 |
|  | INX 1098 |  |  |  |  |  |  |  |  |  |  |
|  | IF168 |  |  |  |  |  |  |  |  |  |  |
|  | TPS |  |  |  |  |  |  |  |  |  |  |
|  | GS |  |  |  |  |  |  |  |  |  |  |

|  |  | A-11 | A-12 | A-13 | A-14 | A-15 | A-16 | A-17 | A-18 | A-19 |
|---|---|---|---|---|---|---|---|---|---|---|
| Elastomers | PE1 | 80 | 80 | 80 | 80 | 80 | 80 | 80 | 80 | 80 |
|  | PE2 |  |  |  |  |  |  |  |  |  |
|  | PE3 |  |  |  |  |  |  |  |  |  |
|  | PU1 |  |  |  |  |  |  |  |  |  |
|  | PU2 | 20 | 20 | 20 | 20 | 20 | 20 | 20 | 20 | 20 |
|  | PU3 |  |  |  |  |  |  |  |  |  |
|  | PA1 |  |  |  |  |  |  |  |  |  |
| Chain extender | PBO |  |  | 0.5 |  |  | 0.5 | 0.5 | 0.5 | 0.5 |
|  | LA-1 |  |  |  |  |  |  |  |  |  |
|  | SBXL P |  |  |  |  |  |  |  |  |  |
|  | HMDI |  |  |  | 0.5 |  |  |  |  |  |
|  | TPA-100 |  | 0.5 |  |  |  |  |  |  |  |
|  | JER1010 |  |  |  |  | 0.5 |  |  |  |  |
|  | MA | 0.5 |  |  |  |  |  |  |  |  |
| Catalyst | DABCO | 0.05 |  |  |  |  | 0.05 | 0.05 | 0.05 | 0.05 |
|  | DBTDL |  | 0.05 |  |  |  |  |  |  |  |
| Heating stabilizer | TIN770 | 1.0 | 1.0 | 1.0 | 1.0 | 1.0 |  |  |  |  |
|  | INX 1098 |  |  |  |  |  | 1.0 |  |  |  |
|  | IF168 |  |  |  |  |  |  | 1.0 |  |  |
|  | TPS |  |  |  |  |  |  |  | 1.0 |  |
|  | GS |  |  |  |  |  |  |  |  | 1.0 |

TABLE I-1-2

Resin for second layer (outer layer) (continued)

|  |  | A-20 | A-21 | A-22 | Ac-1 | Ac-2 | Ac-3 | Ac-4 | Ac-5 | Ac-6 |
|---|---|---|---|---|---|---|---|---|---|---|
| Elastomers | PE1 | 80 | 80 | 80 | 80 | 100 | 80 | 80 | 70 | 100 |
|  | PE2 |  |  |  |  |  |  |  |  |  |
|  | PE3 |  |  |  |  |  |  |  | 30 |  |
|  | PU1 |  |  |  |  |  |  |  |  |  |
|  | PU2 | 20 | 20 | 20 | 20 |  | 20 | 20 |  |  |
|  | PU3 |  |  |  |  |  |  |  |  |  |

TABLE I-1-2-continued

| | | Resin for second layer (outer layer) (continued) | | | | | | | | |
|---|---|---|---|---|---|---|---|---|---|---|
| | | A-20 | A-21 | A-22 | Ac-1 | Ac-2 | Ac-3 | Ac-4 | Ac-5 | Ac-6 |
| Chain extender | PA1 | | | | | | | | | |
| | PBO | 1.5 | 0.2 | 0.05 | | | | | | 0.5 |
| | LA-1 | | | | | | | | 2.0 | |
| | SBXL P | | | | | | | | | |
| | HMDI | | | | | | | | | |
| | TPA-100 | | | | | | | | | |
| | JER1010 | | | | | | | | | |
| | MA | | | | | | | | | |
| Catalyst | DABCO | 0.05 | 0.05 | 0.05 | | | 0.05 | | | 0.05 |
| | DBTDL | | | | | | | 0.05 | | |
| Heating stabilizer | TIN770 | 1.0 | 1.0 | 1.0 | 1.0 | 1.0 | 1.0 | 1.0 | 1.0 | 1.0 |
| | INX 1098 | | | | | | | | | |
| | IF168 | | | | | | | | | |
| | TPS | | | | | | | | | |
| | GS | | | | | | | | | |

PBO: 2,2'-(1,3-phenylene)-bis(2-oxazoline)

LA-1: Carbodilite LA-1 (manufactured by Nisshinbo Holdings Inc.)

SBXL P: Stabaxol P (manufactured by Japan Stabaxol Inc.)

HMDI: 1,6-hexamethylene diisocyanate

TPA-100: Duranate TPA-100 (manufactured by Asahi Kasei Chemicals Corp.)

JER1010: Oligomer type epoxy resin JER1010 (manufactured by Mitsubishi Chemical Corp.)

MA: Maleic anhydride

DABCO: 1,4-diazabicyclo[2.2.2]octane

DBTDL: Dibutyl tin dilaurate

TIN770: Tinuvin 770DF (manufactured by BASF Corp.)

INX 1098: Irganox 1098 (manufactured by BASF Corp.)

IF168: Irgafox 168 (manufactured by BASF Corp.)

TPS: Sumilizer TPS (manufactured by Sumitomo Chemical Co., Ltd.)

GS: Sumilizer GS (manufactured by Sumitomo Chemical Co., Ltd.)

Polyester elastomers (D hardness: JIS K 7215 is inside the brackets)

PE1: Hytrel 4767 manufactured by Du Pont-Toray Co., Ltd. (47 D) (weight average molecular weight: 114,000)

PE2: Pelprene P-40H manufactured by Toyobo Co., Ltd. (38 D) (weight average molecular weight: 132,000)

PE3: Arnitel EM400 manufactured by DSM Corp. (34 D) (weight average molecular weight: 121,000)

PE4: Hytrel 3046 manufactured by Du Pont-Toray Co., Ltd. (27 D) (weight average molecular weight: 128,000)

Polyurethane elastomers (the D hardness: JIS K 7215 is inside the brackets)

PU1: Pandex T-2190 manufactured by DIC Bayer Polymer Ltd. (92 A) (weight average molecular weight: 189,000)

PU2: Elastollan ET1080 manufactured by BASF Corp. (80 A) (weight average molecular weight: 124,000)

PU3: Miractran E675 MNAT produced by Nippon Miractran Co., Ltd. (75 A) (weight average molecular weight: 217,000)

PU4: Pandex T-5865 manufactured by DIC Bayer Polymer Ltd. (65 A) (weight average molecular weight: 172,000)

Polyamide elastomers (the D hardness: JIS K 7215 is inside the brackets)

PA1: Pebax 2533 manufactured by Arkema Co., Ltd. (84 A) (weight average molecular weight: 208,000)

PA2: Pebax 3533 manufactured by Arkema Co., Ltd. (75 A) (weight average molecular weight: 171,000)

TABLE I-2

| | | Resin for first layer (inner layer) | | | | |
|---|---|---|---|---|---|---|
| | | B-1 | B-2 | B-3 | B-4 | B-5 |
| Elastomers | PE4 | | 30 | | | |
| | PU4 | 100 | 70 | 100 | 100 | |
| | PA2 | | | | | 100 |
| Chain extender | PBO | | 0.2 | | | |
| | LA-1 | | | | | 0.2 |
| | TPA-100 | | | 0.2 | 0.2 | |
| | JER1010 | | | | | |
| Catalyst | DABCO | | 0.02 | 0.02 | | |
| | DBTDL | | | | 0.02 | |
| Heating stabilizer | TIN770 | 1.0 | 1.0 | 1.0 | 1.0 | 1.0 |

TABLE I-3-1

| No. | Outer layer | Inner layer | Ratio (front end) | Ratio (rear end) | Solubility | Peracetic acid resistance | Flexibility | Elasticity | Torsion torque | Bending durability | Temperature dependency | Top coat adhesion |
|---|---|---|---|---|---|---|---|---|---|---|---|---|
| 101 | A-1 | B-1 | 20:80 | 80:20 | A | A | A | A | 0.06 | A | A | A |
| 102 | A-2 | B-1 | 20:80 | 80:20 | A | A | A | A | 0.07 | A | B | A |
| 103 | A-3 | B-1 | 20:80 | 80:20 | A | A | A | A | 0.08 | A | B | A |
| 104 | A-4 | B-1 | 20:80 | 80:20 | A | A | A | A | 0.06 | A | A | B |
| 105 | A-5 | B-1 | 20:80 | 80:20 | A | A | A | A | 0.06 | B | A | B |
| 106 | A-6 | B-1 | 20:80 | 80:20 | A | A | B | AA | 0.06 | B | A | A |
| 107 | A-7 | B-1 | 20:80 | 80:20 | A | A | B | AA | 0.06 | B | A | A |
| 108 | A-8 | B-1 | 20:80 | 80:20 | A | A | A | A | 0.08 | A | A | AA |
| 109 | A-9 | B-1 | 20:80 | 80:20 | A | A | B | A | 0.09 | A | A | AA |
| 110 | A-10 | B-1 | 20:80 | 80:20 | A | A | A | A | 0.06 | B | A | A |
| 111 | A-11 | B-1 | 20:80 | 80:20 | A | A | B | A | 0.07 | B | A | A |
| 112 | A-12 | B-1 | 20:80 | 80:20 | A | A | B | A | 0.09 | A | A | AA |

TABLE I-3-1-continued

| No. | Outer layer | Inner layer | Ratio (front end) | Ratio (rear end) | Solubility | Peracetic acid resistance | Flexibility | Elasticity | Torsion torque | Bending durability | Temperature dependency | Top coat adhesion |
|---|---|---|---|---|---|---|---|---|---|---|---|---|
| 113 | A-13 | B-1 | 20:80 | 80:20 | A | B | A | A | 0.09 | B | A | A |
| 114 | A-14 | B-1 | 20:80 | 80:20 | A | B | A | A | 0.08 | B | A | AA |
| 115 | A-15 | B-1 | 20:80 | 80:20 | A | B | A | A | 0.06 | B | A | A |
| 116 | A-16 | B-1 | 20:80 | 80:20 | A | A | A | A | 0.06 | A | A | A |
| 117 | A-17 | B-1 | 20:80 | 80:20 | A | A | A | A | 0.06 | A | A | B |
| 118 | A-18 | B-1 | 20:80 | 80:20 | A | B | A | A | 0.06 | A | A | A |
| 119 | A-19 | B-1 | 20:80 | 80:20 | A | A | A | A | 0.06 | A | A | A |
| 120 | A-20 | B-1 | 20:80 | 80:20 | A | A | B | A | 0.06 | B | A | A |
| 121 | A-21 | B-1 | 20:80 | 80:20 | A | A | A | A | 0.06 | A | A | A |
| 122 | A-22 | B-1 | 20:80 | 80:20 | A | B | A | A | 0.06 | A | A | A |

TABLE I-3-2

| No. | Outer layer | Inner layer | Ratio (front end) | Ratio (rear end) | Solubility | Peracetic acid resistance | Flexibility | Elasticity | Torsion torque | Bending durability | Temperature dependency | Top coat adhesion |
|---|---|---|---|---|---|---|---|---|---|---|---|---|
| 201 | A-1 | B-2 | 20:80 | 80:20 | A | A | B | AA | 0.05 | A | A | B |
| 202 | A-1 | B-3 | 20:80 | 80:20 | A | A | A | A | 0.08 | A | A | A |
| 203 | A-1 | B-4 | 20:80 | 80:20 | A | A | A | A | 0.08 | A | A | A |
| 204 | A-1 | B-5 | 20:80 | 80:20 | A | A | A | A | 0.06 | B | AA | A |
| 205 | A-1 | B-1 | 10:90 | 90:10 | A | A | A | A | 0.08 | A | A | A |
| 206 | A-1 | B-1 | 30:70 | 90:10 | A | A | B | A | 0.06 | A | A | A |
| 207 | A-1 | B-1 | 35:65 | 65:35 | A | A | B | B | 0.06 | A | A | A |
| 208 | A-6 | B-5 | 20:80 | 80:20 | A | AA | A | A | 0.08 | A | AA | B |
| 209 | B-1 | A-1 | 20:80 | 80:20 | A | A | A | A | 0.08 | A | A | AA |
| C11 | A-1 | — | 100:0 | 100:0 | A | A | C | A | 0.04 | A | A | B |
| C12 | — | B-1 | 0:100 | 0:100 | A | A | A | C | 0.22 | A | C | AA |
| C13 | Ac-1 | B-1 | 20:80 | 80:20 | A | A | C | A | 0.12 | C | A | A |
| C14 | Ac-2 | B-1 | 20:80 | 80:20 | A | C | B | AA | 0.10 | C | A | B |
| C15 | Ac-3 | B-1 | 20:80 | 80:20 | A | C | A | A | 0.12 | C | A | A |
| C16 | Ac-4 | B-1 | 20:80 | 80:20 | A | C | A | A | 0.12 | C | A | A |
| C17 | Ac-5 | B-1 | 20:80 | 80:20 | A | AA | C | B | 0.06 | D | A | A |
| C18 | Ac-5 | — | 100:0 | 100:0 | C | A | C | A | 0.05 | D | A | B |
| C19 | Ac-6 | B-1 | 20:80 | 80:20 | A | C | B | AA | 0.05 | C | A | C |

The bolded underlined portions indicate comparative components or inferior data.
Test Nos. starting with "C" are comparative examples.

Unless otherwise stated, the tests below were performed under a 50% RH environment at 25° C. (normal temperature).

[Solubility of Resin Layer in HFIP]

0.2 g of a resin was peeled from a flexible tube after a molding process, immersed in 5 ml of 1,1,1,3,3,3-hexafluoro-2-propanol at room temperature, and it was confirmed by visual observation whether or not there was a residue after being left for 4 hours.

A: Residue was not visible at all
C: Residue was visible

Peracetic Acid Resistance

The resin was peeled from the flexible tube described above, made into test pieces by being cut to a size of 1 cm×10 cm and dried for 24 hours at 23° C.×50% RH after being dipped in 0.3% peracetic acid solution at 50° C. for 150 hours and being cleared with water thoroughly the surfaces thereof, and then a tension test with 50% extensibility was performed using Tensilon.

AA: Not ruptured in a tension test with 150% extensibility
A: Not ruptured in a tension test with 50% extensibility
B: Not ruptured in a tension test with 50% extensibility but detachment occurred between layers
C: Ruptured in a tension test with 50% extensibility Flexibility A position at 40 cm and a position at 20 cm from the tip portion of the flexible tube were fixed, a position at 30 cm was pushed in 15 mm, and the repelling force after 30 seconds was measured by a force gauge.

A: Impact resilience is 15 N or less
B: Over 15 N to 25 N or less
C: Over 25 N

Elasticity

A position at 70 cm and a position at 50 cm from the tip portion of the flexible tube were fixed, a position at 60 cm (a central section of the flexible tube) was pushed in 15 mm, and a ratio of the repelling force (B) after 30 seconds with respect to the repelling force (A) after 0.1 second was measured as the elasticity (%).

$$[\text{Elasticity }(\%)] = (B)/(A) \times 100$$

AA: Elasticity is 85% or more
A: 80% or more and less than 85%
B: 70% or more and less than 80%
C: Less than 70%

Torsion Torque

The obtained flexible tube described above was arranged on a table in a U shape so as to have a radius of 20 cm in a curvature section, a torque meter was attached to the tip portion (a soft side), the rear end section (a hard side) was rotated 360° at a constant speed, and the maximum value of the values indicated by the torque meter was set to the torsion torque. It was determined that torsion conformance was more favorable as the torsion torque was lower and, in particular, it was determined that the torsion conformance was favorable at 0.1 Nm or less, a failure when exceeding 0.1 Nm, and a remarkable failure when exceeding 0.2 Nm.

Bending Durability

The obtained flexible tube described above was hooked to a semi-circular portion on a upper portion of a pulley with a 10 cm diameter so as to form a U shape, the tube was reciprocated 10,000 times by pulling alternately the tip portion and the rear end portion of the tube such that the tip portion and the rear end portion came to a high position 5 cm short of the lowest point of the pulley, and the state of the resin was visually observed.

A: Splitting or peeling of the resin was not visible
B: Peeling was visible in a part
C: Peeling was visible in many parts
D: Substantially the entire surface was peeled Temperature Dependency The elasticity test described above was performed under a 50% RH environment at 40° C. and the ratio of elasticity (X) at 25° C. and elasticity (Y) at 40° C. was obtained by the following formula.

$$[\text{Temperature dependency (\%)}]=(Y)/(X)\times 100$$

AA: Temperature dependency is 95% or more and less than 105%
A: 90% or more and less than 95%, or 105% or more and less than 110%
B: 85% or more and less than 90%, or 110% or more and less than 115%
C: Less than 85% or 115% or more Top Coat Adhesion Strength A resin layer was peeled from the obtained flexible tube described above, urethane coating materials (Neo paint urethane #7000 AB (two liquid type) manufactured by Asia Industry Co., Ltd., blended such that the main agent to curing agent weight ratio was 100:5) which were diluted with an MEK solvent were coated on an outside surface of the resin layer, the MEK was volatilized at 50° C. for 30 minutes, the obtained resin layer was so stuck on the other resin layer obtained by peeling from the obtained flexible tube described above that the outside surfaces thereof were opposed to each other and subsequently heated and cured at 130° C. for 4 hours, and a multi-layer sheet which sandwiched a urethane-based top coat (approximately thickness of 50 μm) was produced. A 180° detachment test was performed for an upper resin layer and a lower resin layer of the obtained multiple layer sheet using Tensilon and top coat adhesion strength was measured.

AA: The adhesion strength was sufficiently strong and aggregated detachment occurred in a resin layer or inside a top coat layer
A: Detachment occurred at an interface but the adhesion strength exceeded 4 N/cm
B: Detachment occurred at an interface but the adhesion strength was 2 N/cm or more and less than 4 N/cm
C: Less than 2 N/cm Using a resin according to the first invention and introducing the resin into the consecutive molding machine shown in FIGS. 3 and 4, a flexible tube for an endoscope was produced. In detail, a first layer resin (an inner layer) in Table 2 and a second layer resin (an outer layer) in Table I-1 were coated in this order on a flexible tube base with a diameter of 12.0 mm. The thickness of the resin layer is 0.4 mm and the inner and outer layer ratio of the front end and the rear end was set to 10:90 to 90:10. Using the obtained flexible tube, a model test was carried out supposing a diagnosis of a body cavity. As a result, the endoscope on which a flexible tube which has a resin layer of the Example is mounted exhibited favorable operability and cleaning resistance with little temperature dependency.

Example II

Example According to Second Invention

Example II-1 and Comparative Example II-1

Resin mixtures (a resin mixture for each of the outer layer and inner layer) were prepared with the blends (parts by mass) described in Tables II-1 and II-2 below, a melt-kneading process was performed at a screw rotation speed of 100 rpm at a barrel setting temperature of 210° C. using a double axis kneading machine manufactured by Technovel Corp. (product name: KZW15-30MG), discharged resin strands in melted state were cooled in a water tank, and then samples in pellet form were manufactured by a pelletizer.

Figure 3:
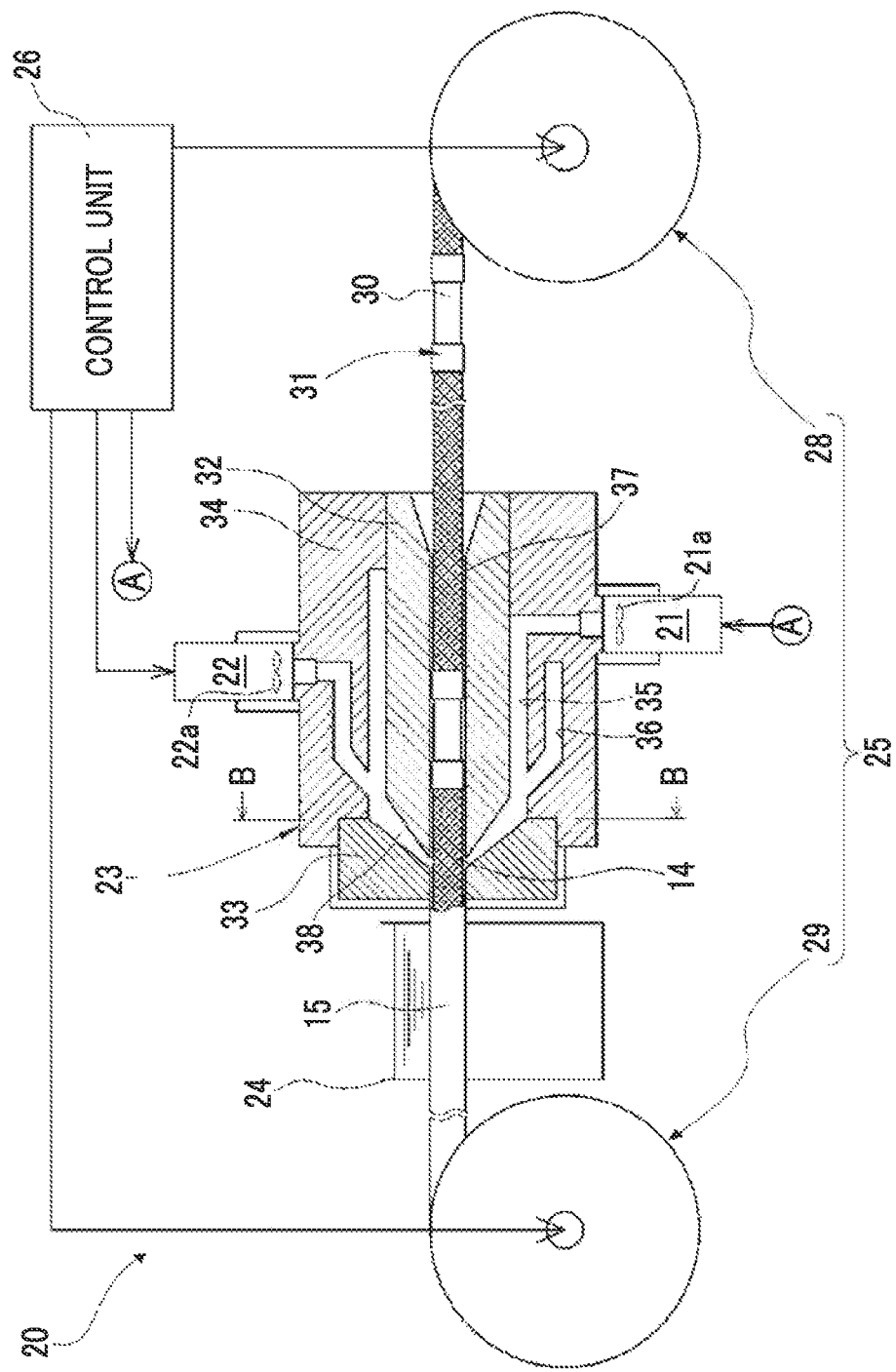
FIG. 3 is a block diagram which schematically shows a configuration of a production apparatus of a flexible tube for an endoscope.
Figure 4:
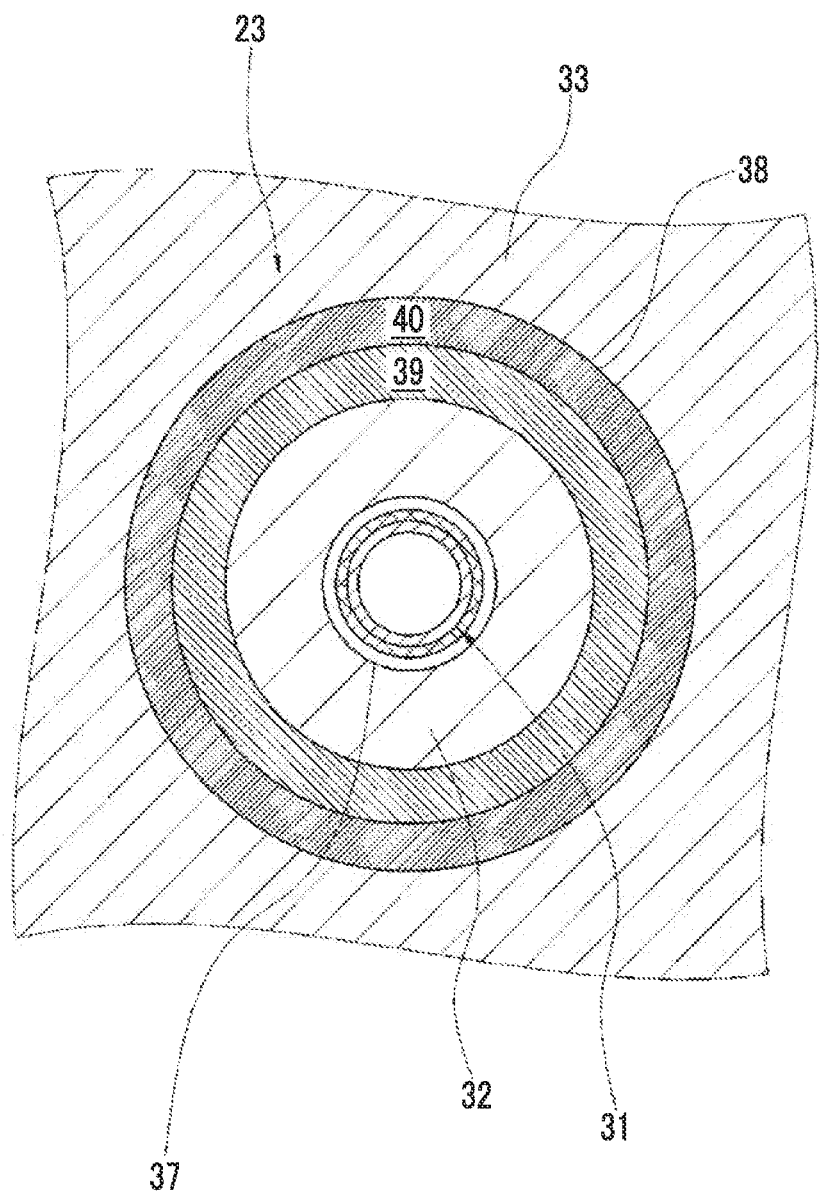
FIG. 4 is a sectional diagram cut away along the B-B line in FIG. 3.

Using the resins shown in Tables II-1 and II-2 and introducing the resins into the consecutive molding machine shown in FIGS. 3 and 4, a flexible tube for an endoscope was produced. In detail, a resin mixture for an inner layer in Table 2 (a composition) and a resin mixture for an outer layer in Table 1 (a composition) were coated in this order on a flexible tube base with a diameter of 12.0 mm and a length of 120 cm. The thickness of the resin layer was 0.4 mm and the inner and outer layer ratios of the front end and the rear end were as described in Table II-3 below. Using the obtained flexible tube, the following tests were performed. The results are shown in Table II-3.

Unless otherwise stated, the tests below were performed under a 50% RH environment at 25° C. (normal temperature).

Peracetic Acid Resistance

The resin was peeled from the flexible tube described above, made into test pieces by being cut to a size of 1 cm×10 cm and dried for 24 hours at 23° C.×50% RH after being dipped in 0.3% peracetic acid solution at 50° C. for 150 hours and being cleared with water thoroughly the surfaces thereof, and then a tension test with 50% extensibility was performed using Tensilon.

AA: Not ruptured in a tension test with 150% extensibility
A: Not ruptured in a tension test with 50% extensibility
B: Not ruptured in a tension test with 50% extensibility but detachment occurred between layers
C: Ruptured in a tension test with 50% extensibility Hydrogen Peroxide Water Resistance The resin was peeled from the flexible tube described above, made into test pieces by being cut to a size of 1 cm×10 cm and dried for 24 hours at 23° C.×50% RH after being dipped in 7.0% hydrogen peroxide water at 55° C. for 150 hours and being cleared with water thoroughly the surfaces thereof, and then a tension test with 50% extensibility was performed using Tensilon.

AA: Not ruptured in a tension test with 150% extensibility
A: Not ruptured in a tension test with 50% extensibility
B: Not ruptured in a tension test with 50% extensibility but detachment occurred between layers
C: Ruptured in a tension test with 50% extensibility Flexibility A position at 40 cm and a position at 20 cm from the tip portion of the flexible tube were fixed, a position at 30 cm was pushed in 15 mm, and the repelling force after 30 seconds was measured by a force gauge.

A: Impact resilience is 15 N or less
B: Over 15 N to 25 N or less
C: Over 25 N

Elasticity

A position at 70 cm and a position at 50 cm from the tip portion were fixed of the flexible tube, a position at 60 cm (a central section of the flexible tube) was pushed in 15 mm, and a ratio of the repelling force (B) after 30 seconds with respect to the repelling force (A) after 0.1 second was measured as the elasticity (%).

[Elasticity (%)]=(*B*)/(*A*)×100

A: The elasticity was 80% or more
B: 70% or more and less than 80%
C: Less than 70%

Bending Durability

The obtained flexible tube described above was hooked to a semi-circular portion on a upper portion of a pulley with a 10 cm diameter so as to form a U shape, the tube was reciprocated 10,000 times by pulling alternately the tip portion and the rear end portion of the tube such that the tip portion and the rear end portion came to a high position 5 cm short of the lowest point of the pulley, and the state of the resin was visually observed.

A: Splitting or peeling of the resin was not visible
B: Peeling was visible in a part

TABLE II-1-1

| | | \multicolumn{10}{c|}{Resin mixture for an outer layer} |
|---|---|---|---|---|---|---|---|---|---|---|---|
| | | A-1 | A-2 | A-3 | A-4 | A-5 | A-6 | A-7 | A-8 | A-9 | A-10 |
| Elastomers | PE1 | 70 | 70 | 70 | 70 | 70 | 70 | 70 | 70 | 70 | 70 |
| | PE2 | | | | | | | | | | |
| | PE3 | | | | | | | | | | |
| | PU1 | 30 | 30 | 30 | 30 | 30 | 30 | 30 | 30 | 30 | 30 |
| | PU2 | | | | | | | | | | |
| | PU3 | | | | | | | | | | |
| | PA1 | | | | | | | | | | |
| HP | HP-1 | 1.0 | | | | | | | | | |
| | HP-2 | | 1.0 | | | | | | | | |
| | HP-3 | | | 1.0 | | | | | | | |
| HA | HA-1 | | | | 1.0 | | | | | | |
| | HA-2 | | | | | 1.0 | | | | | |
| | HA-3 | | | | | | 1.0 | | | | |
| | HA-4 | | | | | | | 1.0 | | | |
| | HA-5 | | | | | | | | 1.0 | | |
| | HA-6 | | | | | | | | | 1.0 | |
| | HA-7 | | | | | | | | | | 1.0 |
| Heating stability (Min) | | 139 | 134 | 136 | 101 | 112 | 113 | 101 | 115 | 117 | 101 |
| | | A-11 | A-12 | A-13 | A-14 | A-15 | A-16 | A-17 | A-18 | A-19 | A-20 |
| Elastomers | PE1 | 70 | 70 | 70 | 70 | 70 | 70 | 70 | 70 | 70 | 70 |
| | PE2 | | | | | | | | | | |
| | PE3 | | | | | | | | | | |
| | PU1 | 30 | 30 | 30 | 30 | 30 | 30 | 30 | 30 | 30 | 30 |
| | PU2 | | | | | | | | | | |
| | PU3 | | | | | | | | | | |
| | PA1 | | | | | | | | | | |
| HP | HP-1 | 0.5 | 0.5 | 0.5 | 0.5 | 0.5 | 0.5 | 0.5 | 0.005 | 0.1 | 3.0 |
| | HP-2 | | | | | | | | | | |
| | HP-3 | | | | | | | | | | |
| HA | HA-1 | 0.5 | | | | | | | 0.5 | 0.5 | 0.5 |
| | HA-2 | | 0.5 | | | | | | | | |
| | HA-3 | | | 0.5 | | | | | | | |
| | HA-4 | | | | 0.5 | | | | | | |
| | HA-5 | | | | | 0.5 | | | | | |
| | HA-6 | | | | | | 0.5 | | | | |
| | HA-7 | | | | | | | 0.5 | | | |
| Heating stability (Min) | | 120 | 148 | 126 | 120 | 149 | 128 | 120 | 107 | 120 | 126 |

TABLE II-1-2

Resin mixture for an outer layer (continued)

| | | A-21 | A-22 | A-23 | A-24 | A-25 | A-26 | A-27 | A-28 | A-29 | A-30 |
|---|---|---|---|---|---|---|---|---|---|---|---|
| Elastomers | PE1 | 70 | 70 | 70 | 70 | 70 | 70 | 70 | 100 | 85 | 50 |
| | PE2 | | | | | | | | | | |
| | PE3 | | | | | | | | | | |
| | PU1 | 30 | 30 | 30 | 30 | 30 | 30 | 30 | | 15 | 50 |
| | PU2 | | | | | | | | | | |
| | PU3 | | | | | | | | | | |
| | PA1 | | | | | | | | | | |
| HP | HP-1 | 5.0 | 8.0 | 0.5 | 0.5 | 0.5 | 0.5 | 0.5 | 0.5 | 0.5 | 0.5 |
| | HP-2 | | | | | | | | | | |
| | HP-3 | | | | | | | | | | |
| HA | HA-1 | 0.5 | 0.5 | 0.005 | 0.1 | 3.0 | 5.0 | 8.0 | 0.5 | 0.5 | 0.5 |
| | HA-2 | | | | | | | | | | |
| | HA-3 | | | | | | | | | | |
| | HA-4 | | | | | | | | | | |
| | HA-5 | | | | | | | | | | |
| | HA-6 | | | | | | | | | | |
| | HA-7 | | | | | | | | | | |
| Heating stability (Min) | | 124 | 123 | 138 | 136 | 110 | 101 | 98 | 132 | 131 | 105 |

| | | A-31 | A-32 | A-33 | A-34 | A-c1 | A-c2 | A-c3 | A-c4 | A-c5 | A-c6 |
|---|---|---|---|---|---|---|---|---|---|---|---|
| Elastomers | PE1 | 30 | 70 | 70 | 70 | | | | | | 70 |
| | PE2 | | | | | | | | | | |
| | PE3 | | | | | | | | | | |
| | PU1 | 70 | | | | 100 | | 100 | 100 | | 30 |
| | PU2 | | 30 | | | | | | | | |
| | PU3 | | | | 30 | | | | | | |
| | PA1 | | | 30 | | | 100 | | | 100 | |
| HP | HP-1 | 0.5 | 0.5 | 0.5 | 0.5 | 0.5 | 0.5 | 0.5 | | 0.5 | |
| | HP-2 | | | | | | | | | | |
| | HP-3 | | | | | | | | | | |
| HA | HA-1 | 0.5 | 0.5 | 0.5 | 0.5 | 0.5 | 0.5 | | 0.5 | | |
| | HA-2 | | | | | | | | | | |
| | HA-3 | | | | | | | | | | |
| | HA-4 | | | | | | | | | | |
| | HA-5 | | | | | | | | | | |
| | HA-6 | | | | | | | | | | |
| | HA-7 | | | | | | | | | | |
| Heating stability (Min) | | 92 | 132 | 132 | 128 | 80 | 130 | 84 | 78 | 130 | 45 |

TABLE II-2

Resin mixture for an inner layer

| | | B-1 | B-2 | B-3 | B-4 | B-5 | B-6 |
|---|---|---|---|---|---|---|---|
| Elastomers | PE4 | | 30 | | | | |
| | PU4 | 100 | 70 | | 100 | 100 | 100 |
| | PA2 | | | 100 | | | |
| HP | HP-1 | 0.5 | 0.5 | 0.5 | 0.5 | | |
| HA | HA-1 | 0.5 | 0.5 | 0.5 | | 0.5 | |

Description of Technical Terms in Tables

Polyester elastomers (D hardness: JIS-K7215 is inside the brackets)

PE1: Hytrel 4047 manufactured by Du Pont-Toray Co., Ltd. (40 D) (weight average molecular weight: 123,000, 100% modulus 25 MPa)

PE2: Pelprene P-40H manufactured by Toyobo Co., Ltd. (38 D) (weight average molecular weight: 132,000, 100% modulus 17 MPa)

PE3: Arnitel EM400 manufactured by DSM Corp. (34 D) (weight average molecular weight: 121,000, 100% modulus 12 MPa)

PE4: Hytrel 3046 manufactured by Du Pont-Toray Co., Ltd. (27 D) (weight average molecular weight: 128,000, 100% modulus 8.0 MPa)

Polyurethane elastomers (D hardness: JIS-K7215 is inside the brackets)

PU1: Pandex T-2190 manufactured by DIC Bayer Polymer Ltd. (92 A) (weight average molecular weight: 189,000, 100% modulus 11 MPa)

PU2: Elastollan ET1080 manufactured by BASF Corp. (80 A) (weight average molecular weight: 124,000, 100% modulus 5.0 MPa)

PU3: Miractran E675 MNAT produced by Nippon Miractran Co., Ltd. (75 A) (weight average molecular weight: 217,000, 100% modulus 2.9 MPa)

PU4: Pandex T-5865 manufactured by DIC Bayer Polymer Ltd. (65 A) (weight average molecular weight: 172,000, 100% modulus 2.3 MPa)

Polyamide elastomers (D hardness: JIS-K7215 is inside the brackets)

PA1: Pebax 2533 manufactured by Arkema Co., Ltd. (75 A) (weight average molecular weight: 208,000, 100% modulus 4.4 MPa)

PA2: Pebax 3533 manufactured by Arkema Co., Ltd. (83 A) (weight average molecular weight: 171,000, 100% modulus 6.0 MPa)

Hindered Phenol Compounds (HP)
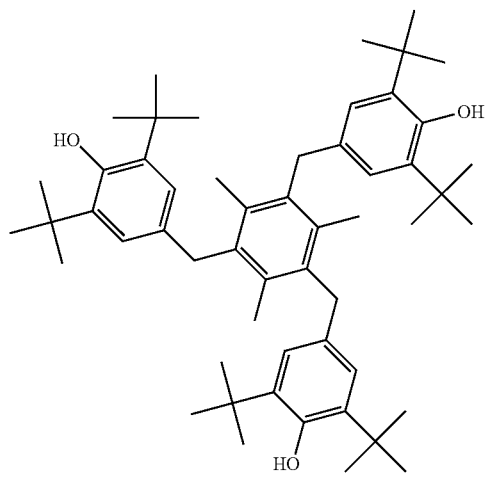
IRG1330: Irganox 1330 (manufactured by BASF Corp.)
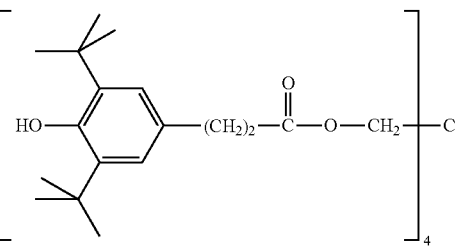
IRG1010: Irganox 1010 (manufactured by BASF Corp.)
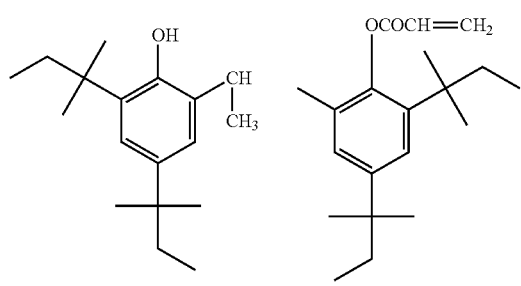
GS: Sumilizer GS (manufactured by Sumitomo Chemical Co., Ltd.)
Hindered amine compounds (HA)
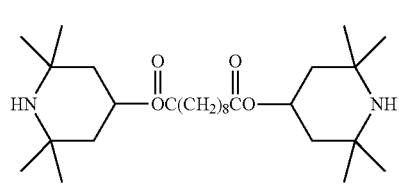
Tinuvin 770DF (manufactured by BASF Corp.)
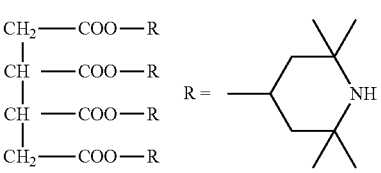
Adekastab LA-57 (manufactured by Adeka Corp.)
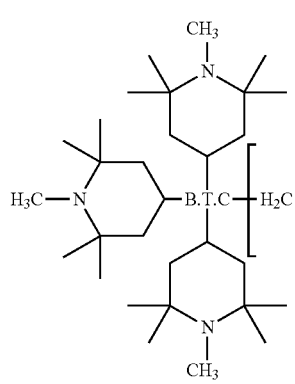
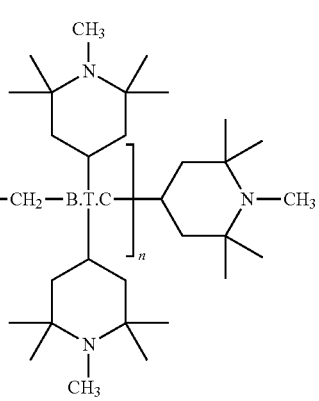
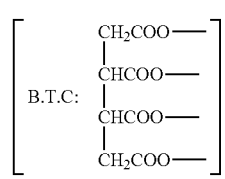

Heating Stability

The time until the weight was reduced by 2% was obtained by keeping the obtained pellet at 220° C. for a certain period of time under nitrogen using TG/DTA.

PH: An example where hindered phenol is not blended is denoted with an "X"

PA: An example where hindered amine is not blended is denoted with an "X"

TABLE II-3-1

| | Outer layer | | | Inner layer | Inner layer: outer layer (front end) | Inner layer: outer layer (front end) | Peracetic acid resistance | Hydrogen peroxide water resistance | Flexibility | Elasticity | Bending durability |
|---|---|---|---|---|---|---|---|---|---|---|---|
| | PE | HP | HA | layer | | | | | | | |
| 101 A-1 | | | X | B-1 | 20:80 | 80:20 | A | B | A | A | A |
| 102 A-2 | | | X | B-1 | 20:80 | 80:20 | A | B | A | A | A |
| 103 A-3 | | | X | B-1 | 20:80 | 80:20 | B | B | A | A | A |
| 104 A-4 | | X | | B-1 | 20:80 | 80:20 | A | A | A | A | A |
| 105 A-5 | | X | | B-1 | 20:80 | 80:20 | A | A | A | A | A |
| 106 A-6 | | X | | B-1 | 20:80 | 80:20 | A | B | A | A | A |
| 107 A-7 | | X | | B-1 | 20:80 | 80:20 | A | B | A | A | A |
| 108 A-8 | | X | | B-1 | 20:80 | 80:20 | A | A | A | A | A |
| 109 A-9 | | X | | B-1 | 20:80 | 80:20 | A | A | A | A | A |
| 110 A-10 | | X | | B-1 | 20:80 | 80:20 | A | B | A | A | A |
| 111 A-11 | | | | B-1 | 20:80 | 80:20 | AA | AA | A | A | A |
| 112 A-12 | | | | B-1 | 20:80 | 80:20 | AA | AA | A | A | A |
| 113 A-13 | | | | B-1 | 20:80 | 80:20 | AA | A | A | A | A |
| 114 A-14 | | | | B-1 | 20:80 | 80:20 | AA | A | A | A | A |
| 115 A-15 | | | | B-1 | 20:80 | 80:20 | AA | AA | A | A | A |
| 116 A-16 | | | | B-1 | 20:80 | 80:20 | AA | AA | A | A | A |
| 117 A-17 | | | | B-1 | 20:80 | 80:20 | AA | A | A | A | A |
| 118 A-18 | | | | B-1 | 20:80 | 80:20 | A | A | A | A | A |
| 119 A-19 | | | | B-1 | 20:80 | 80:20 | AA | A | A | A | A |
| 120 A-20 | | | | B-1 | 20:80 | 80:20 | AA | AA | A | A | A |
| 121 A-21 | | | | B-1 | 20:80 | 80:20 | AA | AA | A | A | A |
| 122 A-22 | | | | B-1 | 20:80 | 80:20 | AA | A | A | B | A |
| 123 A-23 | | | | B-1 | 20:80 | 80:20 | A | B | A | A | A |
| 124 A-24 | | | | B-1 | 20:80 | 80:20 | A | A | A | A | A |
| 125 A-25 | | | | B-1 | 20:80 | 80:20 | AA | AA | A | A | A |
| 126 A-26 | | | | B-1 | 20:80 | 80:20 | AA | AA | A | A | A |
| 127 A-27 | | | | B-1 | 20:80 | 80:20 | AA | AA | A | B | A |
| 128 A-28 | | | | B-1 | 20:80 | 80:20 | AA | AA | B | AA | A |
| 129 A-29 | | | | B-1 | 20:80 | 80:20 | AA | AA | B | A | A |
| 130 A-30 | | | | B-1 | 20:80 | 80:20 | AA | A | A | A | A |

TABLE II-3-2

| No. | Outer layer | | | Inner layer | Inner layer: outer layer (rear end) | Inner layer: outer layer (front end) | Peracetic acid resistance | Hydrogen peroxide water resistance | Flexibility | Elasticity | Bending durability |
|---|---|---|---|---|---|---|---|---|---|---|---|
| | PE | HP | HA | layer | | | | | | | |
| 131 | A-31 | | | B-1 | 20:80 | 80:20 | A | A | A | B | A |
| 132 | A-32 | | | B-1 | 20:80 | 80:20 | AA | AA | A | A | A |
| 133 | A-33 | | | B-1 | 20:80 | 80:20 | AA | AA | A | B | A |
| 134 | A-34 | | | B-1 | 20:80 | 80:20 | AA | A | A | B | B |
| 135 | A-11 | | | B-2 | 20:80 | 80:20 | AA | AA | B | A | A |
| 136 | A-11 | | | B-3 | 20:80 | 80:20 | AA | A | A | A | B |
| 137 | A-11 | | | B-4 | 20:80 | 80:20 | A | A | A | A | A |
| 138 | A-11 | | | B-5 | 20:80 | 80:20 | AA | A | A | A | A |
| 139 | A-11 | | | B-6 | 20:80 | 80:20 | A | A | A | A | A |
| 140 | A-11 | | | B-1 | 10:90 | 90:10 | AA | AA | A | A | A |
| 141 | A-11 | | | B-1 | 30:70 | 90:10 | AA | AA | B | A | A |
| 142 | A-11 | | | B-1 | 35:65 | 65:35 | AA | AA | B | B | A |
| 143 | | A-11 | | | — | — | AA | AA | B | A | A |
| 144 | | A-30 | | | — | — | AA | AA | A | B | A |
| c11 | A-c1 | X | | B-1 | 20:80 | 80:20 | A | B | A | C | A |
| c12 | A-c2 | X | | B-1 | 20:80 | 80:20 | A | B | A | C | B |
| c13 | A-c3 | X | X | B-1 | 20:80 | 80:20 | B | B | A | C | A |
| c14 | A-c4 | X | X | B-1 | 20:80 | 80:20 | A | B | A | C | A |
| c15 | A-c5 | X | | X | B-1 | 20:80 | 80:20 | A | B | A | C | B |
| c16 | A-c6 | | X | X | B-1 | 20:80 | 80:20 | B | C | A | A | A |

Test Nos. starting with "c" are comparative examples.
PE: An example where polyester is not blended is denoted with an "X"

It is understood that with regard to the flexible tube of the present invention and an endoscope which uses the same, a resin layer which coats the flexible tube is provided with characteristics which are required for use in an endoscope type medical device such as flexibility, elasticity, and bending durability and exhibits favorable resistance with respect to various types of disinfectant liquids.

Example II-2

With regard to the flexible tube of Tests No. 111 and 112, a process using peracetic acid and hydrogen peroxide water was performed without peeling off the coated resin. The conditions of the process are the same as those of Example II-1. With respect thereto, a flexible tube test body was created in the same manner apart from changing the inner layer B-1 to B-6, and each test was performed. However, with regard to chemical resistance, evaluation was performed by cutting the flexible tube after chemical treatment. By setting the performance of Tests No. 111 and 112 to Fair and changing the inner layer resin from there, it was confirmed whether improvement (Good) or deterioration (Bad) in the performance was seen. Here, all of the flexibility, elasticity, and bending durability were tested using the flexible tube after the chemical treatment test. With regard to the bending durability, the back and forth rotation speed was set to 25,000 times.

TABLE II-4

| No. | Outer layer | Inner layer | Paracetic acid resistance (outer layer) | Hydrogen peroxide water resistance (outer layer) | Flexibility | Elasticity | Bending durability |
|---|---|---|---|---|---|---|---|
| 111 | A-11 | B-1 | Fair | Fair | Fair | Fair | Fair |
| 111a | A-11 | B-6 | Fair | Fair | Fair | Fair | Good |
| 112 | A-12 | B-1 | Fair | Fair | Fair | Fair | Fair |
| 112a | A-12 | B-6 | Fair | Fair | Fair | Fair | Good |

In Examples according to the second invention, improvement was seen in the bending durability with regard to Examples which did not include hindered amine and hindered phenol in the inner layer as in Table II-4 described above. On the other hand, the chemical resistance was the same in the outer layer and a slight decrease was seen in samples which used B-6 in an inner layer, however, the range was acceptable. In this manner, it is understood that the bending durability of a resin (particularly adhesion between both layers) may be improved while maintaining a sufficient chemical resistance by not including the additive in the inner layer.

Description was given of the present invention along with the embodiments thereof; however, unless otherwise specified, the invention is not limited by any of the fine details of the description and should be widely interpreted without being against the spirit and the range of the invention as shown in attached Claims.

EXPLANATION OF REFERENCES 2 electronic endoscope (endoscope)
3 insertion unit
3a flexible tube
3b angle section
3c tip portion
5 main body operation section
6 universal cord
11 spiral tube
11a metal strip
12 cylindrical net body
13 metal cap
14 flexible tube base
14a front end side
14b base end side
15 resin layer
16 coating film
17 inner layer
18 outer layer
20 consecutive molding machine (production apparatus)
21, 22 extruding section
21a screw
22a screw
23 head section
24 cooling section
25 transport section
26 control unit
30 joint member
31 linking flexible tube base
32 nipple
33 die
34 supporter
35, 36 gate
37 molding path
39 soft resin
40 hard resin

What is claimed is:

1. An endoscope flexible tube having a cylindrical flexible tube base that has flexibility and a resin layer that coats the flexible tube base,
    wherein the resin layer, which is a single layer or multiple layers of two or more layers, comprises a layer A which comprises:
    a resin component, and
    both a hindered phenol compound and a hindered amine compound,
    wherein the resin component comprises polyester elastomers, and at least one of polyurethane elastomers or polyamide elastomers,
    wherein the content of the polyester elastomers in the resin component of the layer A is 55 mass % or more,
    wherein the hindered phenol compounds have structure sites represented by the following Formula (1),

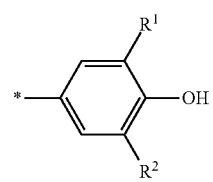

(1)

where, $R^1$ and $R^2$ each independently indicate a hydrogen atom, an alkyl group having 1 to 12 carbon atoms, or an aralkyl group having 7 to 36 carbon atoms, and * indicates a bonding position,
    wherein the hindered amine compounds are compounds which have repeating units represented by Formula (2-2),

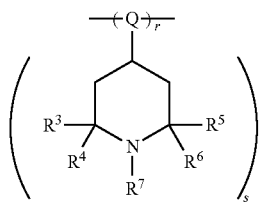 (2-2)

where, $R^3$ to $R^6$ each independently indicate a hydrogen atom or an alkyl group having 1 to 12 carbon atoms, $R^7$ indicates a hydrogen atom, an alkyl group having 1 to 18 carbon atoms, or —$OR^8$, $R^8$ indicates a hydrogen atom or an alkyl group having 1 to 20 carbon atoms, r represents an integer, Q represents an (s+2)-valent linking group, and s represents 1 or 2, and wherein a total amount of the hindered phenol compounds and the hindered amine compounds ranges from 0.01 to 7 parts by mass with respect to 100 parts by mass of the resin component in the layer A of the resin layer.

2. The endoscope flexible tube according to claim 1, wherein the content of the hindered phenol compounds is 0.01 to 5 parts by mass with respect to 100 parts by mass of the resin component in the layer A, and the content of the hindered amine compounds is 0.01 to 5 parts by mass with respect to 100 parts by mass of the resin component in the layer A.

3. The endoscope flexible tube according to claim 2, wherein the hindered phenol compounds are represented by the following Formula (1-1) or (1-2),

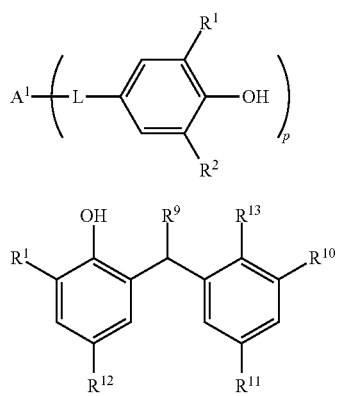

where, $R^1$ and $R^2$ are the same as in Formula (1), L indicates a single bond or a divalent linking group, p indicates an integer of 2 to 4, $A^1$ indicates a divalent to tetravalent linking group, $R^9$ to $R^{12}$ are the same as $R^1$, and $R^{13}$ represents a reactive organic substituent group.

4. The endoscope flexible tube according to claim 1, wherein $R^7$ indicates a hydrogen atom, an unsubstituted alkyl group having 1 to 18 carbon atoms, or —$OR^8$, and $R^8$ indicates a hydrogen atom or an alkyl group having 1 to 20 carbon atoms.

5. The endoscope flexible tube according to claim 1, wherein $R^7$ indicates a hydrogen atom.

6. The endoscope flexible tube according to claim 1, wherein the resin layer is multiple layers and the layer A configures an outermost layer of the resin layer.

7. The endoscope flexible tube according to claim 6, wherein a layer B other than the outermost layer contains at least one resin selected from polyester elastomers, polyurethane elastomers, and polyamide elastomers.

8. The endoscope flexible tube according to claim 7, wherein the content of polyurethane elastomers in a resin component of the layer B is 50 mass % or more.

9. The endoscope flexible tube according to claim 1, wherein a ratio of thicknesses of an inner layer and an outer layer incrementally changes in an axial direction of the flexible tube base with respect to a thickness of the entire resin layer, and a ratio of the thicknesses of the inner layer and the outer layer at one end of the flexible tube base is Inner layer:Outer layer=5:95 to 40:60, a ratio of the thicknesses at another end of the flexible tube base is Inner layer:Outer layer=95:5 to 60:40, and the ratio of the thicknesses is reversed between both ends.

10. The endoscope flexible tube according to claim 1, wherein the content of the polyurethane elastomers in the resin component of the layer A is 5 to 45 mass %.

11. The endoscope flexible tube according to claim 1, having a peracetic acid resistance.

12. The endoscope flexible tube according to claim 1, wherein the content of the polyamide elastomers in the layer A is 0 mass %.

\* \* \* \* \*